United States Patent
Hunt

(10) Patent No.: US 9,636,226 B2
(45) Date of Patent: May 2, 2017

(54) TRAUMATIC BONE FRACTURE REPAIR SYSTEMS AND METHODS

(71) Applicant: 4WEB, Inc., Frisco, TX (US)

(72) Inventor: Jessee Hunt, Plano, TX (US)

(73) Assignee: 4WEB, Inc., Frisco, TX (US)

( * ) Notice: Subject to any disclaimer, the term of this patent is extended or adjusted under 35 U.S.C. 154(b) by 0 days.

(21) Appl. No.: 14/215,961

(22) Filed: Mar. 17, 2014

(65) Prior Publication Data
US 2014/0288649 A1 Sep. 25, 2014

Related U.S. Application Data

(60) Provisional application No. 61/801,524, filed on Mar. 15, 2013.

(51) Int. Cl.
*A61F 2/44* (2006.01)
*A61F 2/30* (2006.01)
(Continued)

(52) U.S. Cl.
CPC .......... *A61F 2/30907* (2013.01); *A61F 2/447* (2013.01); *A61F 2/4611* (2013.01); *A61F 2/2803* (2013.01); *A61F 2002/2835* (2013.01); *A61F 2002/3092* (2013.01); *A61F 2002/3097* (2013.01); *A61F 2002/30153* (2013.01); *A61F 2002/30156* (2013.01); *A61F 2002/30158* (2013.01); *A61F 2002/30179* (2013.01); *A61F 2002/30273* (2013.01); *A61F 2002/30275* (2013.01); *A61F 2002/30278* (2013.01); *A61F 2002/30281* (2013.01); *A61F 2002/30283* (2013.01); *A61F 2002/30599* (2013.01); *A61F 2002/30841* (2013.01); *A61F 2002/30914* (2013.01); *A61F 2002/30943* (2013.01);
(Continued)

(58) Field of Classification Search
CPC .......... A61F 2/4455; A61F 2002/30911; A61F 2002/3092; A61F 2002/30275; A61F 2/30907; A61F 2002/2835; A61F 2002/30153
USPC ..................... 606/246–249; 623/17.11–17.16
See application file for complete search history.

(56) References Cited

U.S. PATENT DOCUMENTS 3,840,904 A 10/1974 Tronzo
3,867,728 A 2/1975 Stubstad et al.
(Continued)

FOREIGN PATENT DOCUMENTS

CN 201164511 12/2008
CN 201200499 3/2009
(Continued)

OTHER PUBLICATIONS

Distension Blog located at htpp://kineticdistensio.blogspot.com/2011_10_0_archive.html including entry of Oct. 14, 2011.
(Continued)

*Primary Examiner* — Mary Hoffman
*Assistant Examiner* — Tara R Carter
(74) *Attorney, Agent, or Firm* — Meyertons, Hood, Kivlin, Kowert & Goetzel, P.C.

(57) ABSTRACT

A hand and/or wrist implant, including a web structure having a space truss with two or more planar truss units having a plurality of struts joined at nodes. The web structure is configured for the repair of traumatic bone fractures.

15 Claims, 24 Drawing Sheets

(51) Int. Cl.
*A61F 2/46* (2006.01)
*A61F 2/28* (2006.01)

(52) U.S. Cl.
CPC .............. *A61F 2002/30945* (2013.01); *A61F 2002/30952* (2013.01); *A61F 2002/30953* (2013.01); *A61F 2002/30957* (2013.01); *A61F 2002/30958* (2013.01); *A61F 2002/30962* (2013.01); *A61F 2002/30968* (2013.01); *A61F 2002/4475* (2013.01); *A61F 2310/00017* (2013.01); *A61F 2310/00023* (2013.01); *A61F 2310/00029* (2013.01); *A61F 2310/00047* (2013.01); *A61F 2310/0097* (2013.01); *A61F 2310/00179* (2013.01); *A61F 2310/00598* (2013.01); *A61F 2310/00796* (2013.01); *A61F 2310/00958* (2013.01); *A61F 2310/00976* (2013.01)

(56) References Cited

U.S. PATENT DOCUMENTS

| | | | |
|---|---|---|---|
| 4,686,970 A | 8/1987 | Dove et al. | |
| 4,820,305 A * | 4/1989 | Harms ................ | A61F 2/2846 606/247 |
| 4,904,261 A | 2/1990 | Dove et al. | |
| 4,938,771 A | 7/1990 | Vecsei et al. | |
| 5,030,233 A | 7/1991 | Ducheyne | |
| 5,147,402 A | 9/1992 | Bohler et al. | |
| 5,201,768 A | 4/1993 | Caspari et al. | |
| 5,282,861 A | 2/1994 | Kaplan | |
| 5,336,266 A | 8/1994 | Caspari et al. | |
| 5,433,750 A | 7/1995 | Gradinger et al. | |
| 5,571,185 A | 11/1996 | Schug | |
| 5,609,635 A | 3/1997 | Michelson | |
| 5,609,637 A | 3/1997 | Biedermann et al. | |
| 5,676,700 A | 10/1997 | Black et al. | |
| 5,702,449 A | 12/1997 | McKay | |
| 5,702,451 A | 12/1997 | Biedermann et al. | |
| 5,879,385 A | 3/1999 | Crockard et al. | |
| 5,897,556 A | 4/1999 | Drewry et al. | |
| 5,954,504 A | 9/1999 | Misch et al. | |
| 5,989,290 A | 11/1999 | Biedermann et al. | |
| 6,010,502 A | 1/2000 | Bagby | |
| 6,143,032 A | 11/2000 | Schafer et al. | |
| 6,149,689 A | 11/2000 | Grundei et al. | |
| 6,206,924 B1 * | 3/2001 | Timm ................ | A61F 2/28 623/17.11 |
| 6,245,110 B1 | 6/2001 | Grundei et al. | |
| 6,264,695 B1 | 7/2001 | Stoy | |
| 6,280,478 B1 | 8/2001 | Richter et al. | |
| 6,290,726 B1 | 9/2001 | Pope et al. | |
| 6,379,385 B1 | 4/2002 | Kalas et al. | |
| 6,464,727 B1 | 10/2002 | Sharkey et al. | |
| 6,585,770 B1 | 7/2003 | White et al. | |
| 6,660,041 B1 | 12/2003 | Grundei | |
| 6,712,852 B1 | 3/2004 | Chung et al. | |
| D493,533 S | 7/2004 | Blain | |
| 6,761,738 B1 | 7/2004 | Boyd | |
| 6,866,682 B1 | 3/2005 | An et al. | |
| 6,881,228 B2 | 4/2005 | Zdeblick et al. | |
| 6,931,812 B1 | 8/2005 | Lipscomb | |
| 6,972,019 B2 | 12/2005 | Michelson | |
| 7,156,874 B2 | 1/2007 | Paponneau et al. | |
| 7,163,560 B2 | 1/2007 | Mason | |
| 7,163,561 B2 | 1/2007 | Michelson | |
| 7,208,222 B2 | 4/2007 | Rolfe et al. | |
| 7,291,149 B1 | 11/2007 | Michelson | |
| 7,572,293 B2 | 8/2009 | Rhodes et al. | |
| 7,578,850 B2 | 8/2009 | Kuczynski et al. | |
| 8,292,967 B2 | 10/2012 | Brown et al. | |
| 8,906,074 B2 * | 12/2014 | Kang ................ | A61B 17/8076 606/283 |
| 8,998,990 B2 | 4/2015 | Bertagnoli et al. | |
| 2004/0082999 A1 | 4/2004 | Mathys et al. | |
| 2004/0121451 A1 | 6/2004 | Mortiz et al. | |
| 2004/0236336 A1 | 11/2004 | Foerster | |
| 2005/0015154 A1 | 1/2005 | Lindsey et al. | |
| 2005/0033425 A1 | 2/2005 | Schwab | |
| 2005/0129726 A1 | 6/2005 | Liebschner | |
| 2005/0143827 A1 | 6/2005 | Globerman et al. | |
| 2005/0171613 A1 | 8/2005 | Sartorius et al. | |
| 2005/0222683 A1 | 10/2005 | Berry | |
| 2006/0106461 A1 | 5/2006 | Embry et al. | |
| 2006/0147332 A1 | 7/2006 | Jones et al. | |
| 2006/0200062 A1 | 9/2006 | Saadat | |
| 2007/0027544 A1 | 2/2007 | McCord et al. | |
| 2007/0032876 A1 | 2/2007 | Clark | |
| 2007/0055376 A1 | 3/2007 | Michelson | |
| 2007/0179610 A1 | 8/2007 | Biedermann et al. | |
| 2007/0233248 A1 | 10/2007 | Schwab et al. | |
| 2007/0255420 A1 | 11/2007 | Johnson et al. | |
| 2007/0270956 A1 | 11/2007 | Heinz | |
| 2008/0014457 A1 | 1/2008 | Gennaro et al. | |
| 2008/0071356 A1 | 3/2008 | Greenhalgh et al. | |
| 2008/0154314 A1 | 6/2008 | McDevitt | |
| 2009/0054987 A1 * | 2/2009 | Chin ................ | A61F 2/447 623/17.16 |
| 2009/0228112 A1 | 9/2009 | Clark et al. | |
| 2010/0106194 A1 | 4/2010 | Bonutti | |
| 2010/0161061 A1 | 6/2010 | Hunt | |
| 2010/0174377 A1 | 7/2010 | Heuer | |
| 2010/0174380 A1 | 7/2010 | Lewis | |
| 2010/0179667 A1 | 7/2010 | Day et al. | |
| 2010/0228355 A1 | 9/2010 | Linares | |
| 2010/0298950 A1 | 11/2010 | McDonnel et al. | |
| 2011/0022180 A1 | 1/2011 | Melkent et al. | |
| 2011/0196495 A1 | 8/2011 | Hunt | |
| 2011/0251690 A1 | 10/2011 | Berger | |
| 2011/0313532 A1 | 12/2011 | Hunt | |
| 2013/0030529 A1 | 1/2013 | Hunt | |
| 2013/0030540 A1 * | 1/2013 | Leibinger ................ | A61F 2/28 623/20.32 |
| 2013/0123935 A1 | 5/2013 | Hunt | |
| 2013/0158672 A1 | 6/2013 | Hunt | |
| 2013/0218282 A1 | 8/2013 | Hunt | |
| 2014/0121776 A1 | 5/2014 | Hunt | |
| 2014/0288649 A1 | 9/2014 | Hunt | |
| 2014/0288650 A1 | 9/2014 | Hunt | |
| 2015/0282933 A1 | 10/2015 | Hunt | |
| 2015/0282945 A1 | 10/2015 | Hunt | |
| 2015/0282946 A1 | 10/2015 | Hunt | |

FOREIGN PATENT DOCUMENTS

| | | |
|---|---|---|
| DE | 19721661 | 11/1998 |
| DE | 102006047663 | 4/2008 |
| EP | 0268115 | 1/1991 |
| EP | 0489684 | 6/1992 |
| WO | 0128460 | 4/2001 |
| WO | 2008022206 | 2/2008 |
| WO | 2010080511 | 7/2010 |

OTHER PUBLICATIONS

Baranovskaya et al. ITECH M. Sc. Programme-Uni Stuttgart, Institut Fur Computerbasiertes Entwerfen (ICD, Stuttgart, Germany located at htpp://architecture-is-yes.tumblr.com/post/8525760 accessed Aug. 21, 2015.
Office Action for U.S. Appl. No. 12/960,092 issued Apr. 22, 2015.
European Examination Report for EP Application No. 09796208.8 dated Feb. 7, 2014.
European Examination Report for EP Application No. 09796208.8 dated Aug. 21, 2014.
Office Action for U.S. Appl. No. 12/818,508 issued May 22, 2015.
Office Action for U.S. Appl. No. 13/805,231 issued Aug. 20, 2015.
Australian Examination Report for AU Application No. 2011267941 dated Jan. 16, 2014.
Japanese Examination Report for JP Application No. 2013-515407 dated Feb. 24, 2015.
Office Action for U.S. Appl. No. 13/194,561 issued Jan. 20, 2015.

(56) References Cited

OTHER PUBLICATIONS

International Preliminary Report on Patentability for PCT/US2012/048300 Feb. 4, 2014.
Office Action for U.S. Appl. No. 13/668,968 issued Jan. 7, 2015.
Office Action for U.S. Appl. No. 13/668,968 issued Jun. 29, 2015.
International Preliminary Report on Patentability for PCT/US2012/063600 issued May 6, 2014.
Supplemental European Search Report for EP Application No. 12846553.1 issued May 20, 2015.
Office Action for U.S. Appl. No. 13/762,825 issued Dec. 12, 2014.
International Preliminary Report on Patentability for PCT/US2013/025281 issued Aug. 12, 2014.
Office Action for U.S. Appl. No. 14/036,974 issued Jul. 22, 2015.
International Preliminary Report on Patentability for PCT/US2013/061725 issued Mar. 13, 2015.
International Search Report and Written Opinion for PCT/US2014/030319 issued Apr. 6, 2015.
Office Action for U.S. Appl. No. 14/216,087 issued Aug. 27, 2015.
"Rapid prototyping enables company to manufacture revolutionary new medical product", accessed at <http://www.newslettersonline.com/user/user.fas/s=63/fp=3/tp=47?T=open_article,565208&P=article>, Oct. 9, 2003. (pp. 1-2).
"Midlantic Medical Systems—Geo Structure Rectangles (Posterior Approach)" accessed Jun. 11, 2008 at <http://www.midlanticmedical.com/products/anteriorColumnSpacers.php?p=2>. (p. 1).
"Midlantic Medical Systems—Nexus (Transverse Approach)" accessed Jun. 11, 2008 at <http://www.midlanticmedical.com/products/anteriorColumnSpacers.php?p=4>. (p. 1).
"Zimmer® Trabecular Metal™ Technology", accessed at <http://www.zimmerindia.com/z/ctl/op/global/action/1/id/9512/template/PC/navid/8173>, Jul. 9, 2006. (pp. 1-5).
"Multifunctional Electrochemical Energy Storage Materials", accessed on Oct. 1, 2008 at <http://www.uvapf.org/technologies/index.cfm/fuseaction/invention/invention_id/85/?CFID=1785971&CFTOKEN=59649784&>. (pp. 1-2).
"Image: C60a.phg", Wikipedia, accessed on Oct. 1, 2008 at <http://en.wikipedia.org/wiki/Image:C60a.png>. (pp. 1-3).
"Image:POV-Ray-Dodecahedron.svg", Wikipedia, accessed at on Oct. 1, 2008 at <http://en.wikipedia.org/wiki/Image:POV-Ray-Dodecahedron.svg>. (pp. 1-4).
"Image:Icosahedron.svg", Wikipedia, accessed on Oct. 1, 2008 at <http://en.wikipedia.org/wiki/Image:Icosahedron.svg>. (pp. 1-2).
"Image:Octahedron.svg", Wikipedia, accessed on Oct. 1, 2008 at <http://en.wikipedia.org/wiki/Image:Octahedron.svg>. (pp. 1-3).
"Truss" Wikipedia, accessed at <http://en.wikipedia.org/wiki/Truss>, Dec. 16, 2009. (pp. 1-9).
"NexGen Trabecular Metal Tibial Cone Augments" accessed at <http://catalog.zimmer.com/content/zpc/products/200/250/C6010E00812653.html>, Nov. 17, 2009. (p. 1).
"Spinal Kinetics", accessed on Oct. 6, 2009 at <http://www.spinalkinetics.com/m6systems.html>. (p. 1).
"CINN", accessed on Oct. 6, 2009 at <http://www.cinn.org/cr-articles/CR-artificial-disc.html>, Copyright 2008. (pp. 1-9).
"Zimmer Anatomical Shoulder Fracture System", copyright 2007. (pp. 1-6).
"Wolff's Law", Wikipedia, accessed at <http://en.wikipedia.org/wiki/Wolff's_law>, Jun. 9, 2010. (pp. 1-2).
"E-Manufacturing is making its inroad to series production", Nov. 20, 2008. (pp. 1-2).
"InFix Anterior Lumbar Device" Dec. 17, 2009. (p. 1).
"Biofoam Wedge System" Wright, Copyright 2010. (pp. 1-4).
"LPT2 Great Toe Implant" Wright, Copyright 2008. (p. 1-16).
"Biofoam Wedge System Surgical Technique" Wright, Copyright 2010. (pp. 1-12).
Murr et al. "Next-generation biomedical implants using additive manufacturing of complex, cellular and functional mesh arrays", Philosophical Transactions of the Royal Society, Mar. 22, 2010, vol. 368, No. 1917, pp. 1999-2032.
Yan, et al. "Mechanical strain regulates osteoblast proliferation through integrin-mediated ERK activation", PloS One, Apr. 23, 2012, vol. 7, No. 4, Article No. e35709.
EPO International Search Report and Written Opinion for PCT/US2009/068512 mailed May 12, 2010. (pp. 1-61).
International Preliminary Report on Patentability for PCT/US2009/068512 dated Mar. 31, 2011. (pp. 1-8).
Australian Examination Report for Australian Patent Application No. 2009335771 dated Jan. 14, 2014.
EPO International Search Report and Written Opinion for PCT/US2011/040117 mailed Aug. 12, 2011.
International Preliminary Report on Patentability for PCT/US2011/040117 dated Dec. 19, 2012.
International Search Report and Written Opinion for PCT/US2012/048300 May 7, 2013.
International Search Report and Written Opinion for PCT/US2012/045717 issued Jan. 30, 2013.
International Preliminary Report on Patentability for PCT/US2012/045717 dated Jan. 7, 2014.
International Search Report and Written Opinion for PCT/US2012/063600 issued Jan. 31, 2013.
International Search Report and Written Opinion for PCT/US2013/025281 issued May 15, 2013.
International Search Report and Written Opinion for PCT/US2013/061725 issued Jan. 13, 2014.
International Search Report and Written Opinion for PCT/US2014/30358 issued Aug. 27, 2014.
Office Action for U.S. Appl. No. 12/640,825 issued Aug. 30, 2012.
Office Action for U.S. Appl. No. 121818,508 issued Feb. 4, 2013.
Final Office Action for U.S. Appl. No. 12/818,508 issued Aug. 15, 2013.
Office Action for U.S. Appl. No. 13/194,561 issued Mar. 19, 2013.
Final Office Action for U.S. Appl. No. 13/194,561 issued Sep. 26, 2013.
Office Action for U.S. Appl. No. 12/960,092 issued Aug. 20, 2014.
Office Action for U.S. Appl. No. 13/668,968 issued Aug. 18, 2014.
Office Action for U.S. Appl. No. 13/762,825 issued Jul. 2, 2014.
Canadian Examination Report for Canadian Patent Application No. 2,746,505 dated Dec. 1, 2015.
Office Action for U.S Appl. No. 14/743,579 issued Apr. 5, 2016.
Office Action for U.S Appl. No. 14/743,607 issued Apr. 6, 2016.
Final Office Action for U.S. Appl. No. 12/818,508 issued Nov. 20, 2015.
Final Office Action for U.S. Appl. No. 13/805,231 issued Dec. 11, 2015.
Japanese Examination Report for JP Application No. 2013-515407 dated Nov. 24, 2015.
Japanese Examination Report for JP Application No. 2014-523976 dated May 24, 2016.
Office Action for U.S Appl. No. 13/668,968 issued Apr. 14, 2016.
Office Action for U.S Appl. No. 13/762,825 issued Mar. 7, 2016.
Chinese Examination Report for CN Application No. 20130055597.3 dated Apr. 5, 2016.

\* cited by examiner

TRAUMATIC BONE FRACTURE REPAIR SYSTEMS AND METHODS

PRIORITY CLAIM

This application claims priority to U.S. Provisional Application Ser. No. 61/801,524 entitled "TRAUMATIC BONE FRACTURE REPAIR SYSTEMS AND METHODS" filed Mar. 15, 2013, which is incorporated herein by reference in its entirety.

BACKGROUND

1. Field of the Invention

The present invention relates generally to medical devices and, more specifically, to implants.

2. Description of the Related Art

Implants may be used in human and/or animals to support and/or secure one or more bones. For example, implants may be used in the spine to support and/or replace damaged tissue between the vertebrae in the spine. Once implanted between two vertebrae, the implant may provide support between the two vertebrae and bone growth may take place around and through the implant to at least partially fuse the two vertebrae for long-term support. Implants may include relatively large rims with solid material that may cover, for example, 50% of the area that interacts with the endplate. The rim may provide a contact area between the implant and the vertebral endplates. Large rims may have several drawbacks. For example, large rims may impede bone growth and reduce the size of the bone column fusing the superior and inferior vertebral bodies.

Spinal implants may include open channels through the center of the supporting rims in a superior/inferior direction. The open channel design may require members of the implant that separate the rims that interact with the vertebral endplates to absorb the compressive forces between the vertebral endplates. This may increase the pressure on smaller areas of the vertebral endplates and may potentially lead to stress risers in the vertebral endplates. Further, while bone graft material is often used in conjunction with implants to encourage bone growth, the open column design of implants may reduce the likelihood of bone graft material from securing itself to the implant which could result in a bio-mechanical cooperation that is not conducive to promoting good fusion.

Bone graft material may be packed into the implant in a high-pressure state to prevent bone graft material from exiting the implant while being placed between the vertebral endplates. The high-pressure state may also reduce the potential for the bone graft material loosening due to motion between the implant and the vertebral endplates or compressive forces experienced during settling of the implant. In addition, a high-pressure environment may allow the bone graft material to re-model and fuse at greater strength. High-pressure states, however, may be difficult to create and maintain for the bone graft material in an implant.

SUMMARY

Various embodiments of implant systems and related apparatus, and methods of operating the same are described herein. In various embodiments, an implant for interfacing with a bone structure includes a web structure, including a space truss, configured to interface with human bone tissue. The space truss includes two or more planar truss units having a plurality of struts joined at nodes.

In an embodiment, an implant for interfacing with a bone structure, includes: a web structure that includes a space truss composed of two or more planar truss units having a plurality of struts joined at nodes, wherein the web structure is configured to interface with human bone tissue; and one or more channels formed in the web structure, the one or more channels extending through the web structure and having an channel exit in at least two sides of the web structure. One or more fasteners are positionable within the channels, wherein the fasteners couple the web structure to a bone during use.

In another embodiment, an implant includes a distal end and a proximate end, wherein the proximal end comprises a space truss comprising two or more planar truss units having a plurality of struts joined at nodes, wherein the space truss is configured to interface with human bone tissue; and wherein the distal end comprises threading which allows the implant to be screwed into a bone structure. In an alternate embodiment, an implant includes a space truss having two or more planar truss units having a plurality of struts joined at nodes, wherein the space truss is configured to interface with human bone tissue; and wherein the exterior of the space truss comprises threading which allows the implant to be screwed into a bone structure.

In another embodiment, an implant includes a space truss having two or more planar truss units having a plurality of struts joined at nodes, and a rod at least partially surrounded by the space truss.

BRIEF DESCRIPTION OF THE DRAWINGS

A better understanding of the present invention may be obtained when the following detailed description is considered in conjunction with the following drawings, in which.

Figure 1A:
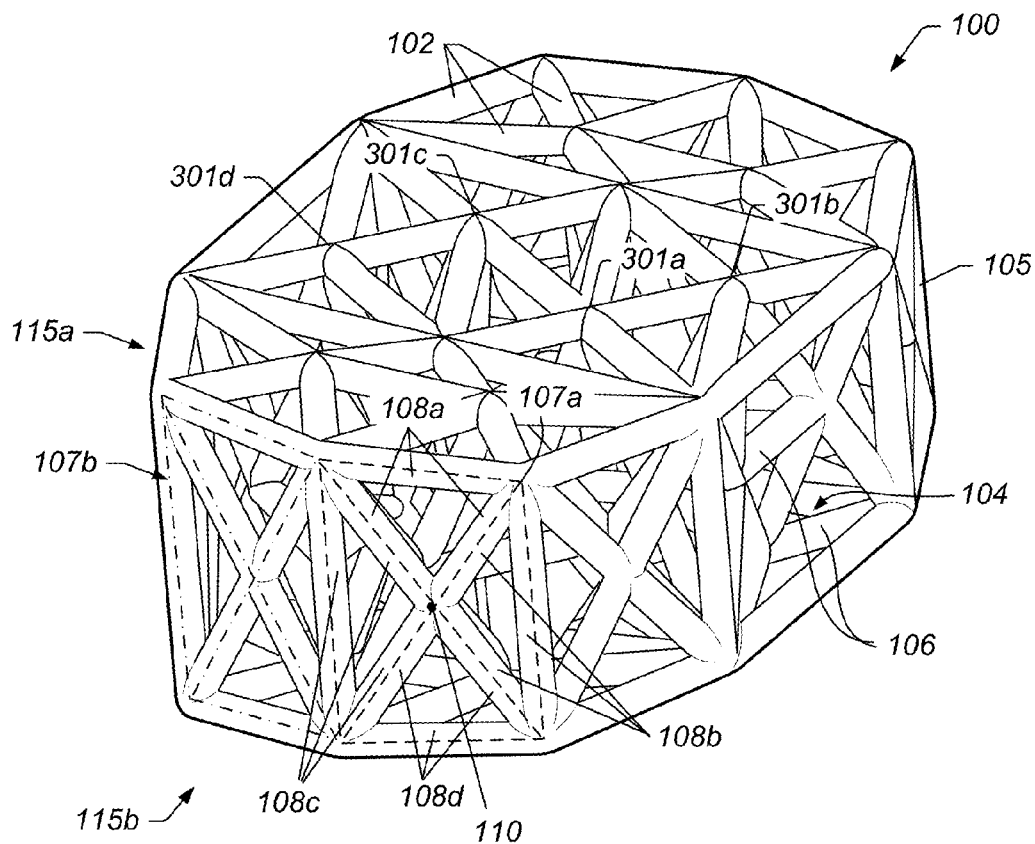
FIGS. 1A-1B illustrate views of an implant with lordosis, according to an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims.

DETAILED DESCRIPTION OF THE EMBODIMENTS

Figure 1B:
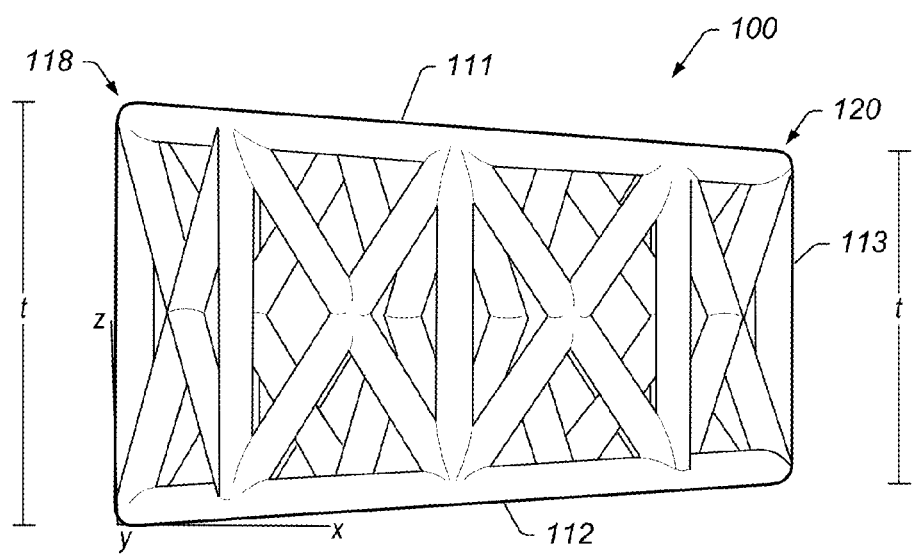

FIGS. 1A-1B illustrate views of implant 100, according to an embodiment. The specifically depicted implant 100 may be used, for example, in anterior lumbar inter-body fusion (ALIF) or posterior lumbar inter-body fusion (PLIF), however, it should be understood that implant 100 may have a variety of shapes suitable for bone fusion applications. In some embodiments, implant 100 may include a web structure with one or more trusses 102 (e.g., planar and space trusses). Implant 100 may be used in various types of implants for humans or animals such as spinal implants, corpectomy devices, knee replacements, hip replacements, long bone reconstruction scaffolding, and cranio-maxifacial implants. Other implant uses are also contemplated.

As used herein a "truss structure" is a structure having one or more elongate struts connected at joints referred to as nodes. Trusses may include variants of a pratt truss, king post truss, queen post truss, town's lattice truss, planar truss, space truss, and/or a vierendeel truss (other trusses may also be used). A "truss unit" is a structure having a perimeter defined by three or more elongate struts."

As used herein a "planar truss" is a truss structure where all of the struts and nodes lie substantially within a single two-dimensional plane. A planar truss, for example, may include one or more "truss units" where each of the struts is a substantially straight member such that the entirety of the struts and the nodes of the one or more truss units lie in substantially the same plane. A truss unit where each of the struts is a substantially straight strut and the entirety of the struts and the nodes of the truss unit lie in substantially the same plane is referred to as a "planar truss unit."

As used herein a "space truss" is a truss having struts and nodes that are not substantially confined in a single two-dimensional plane. A space truss may include two or more planar trusses (e.g., planar truss units) wherein at least one of the two or more planar trusses lies in a plane that is not substantially parallel to a plane of at least one or more of the other two or more planar trusses. A space truss, for example, may include two planar truss units adjacent to one another (e.g., sharing a common strut) wherein each of the planar truss units lie in separate planes that are angled with respect to one another (e.g., not parallel to one another).

As used herein a "triangular truss" is a structure having one or more triangular units that are formed by three straight struts connected at joints referred to as nodes. For example, a triangular truss may include three straight elongate strut members that are coupled to one another at three nodes to from a triangular shaped truss. As used herein a "planar triangular truss" is a triangular truss structure where all of the struts and nodes lie substantially within a single two-dimensional plane. Each triangular unit may be referred to as a "triangular truss unit." A triangular truss unit where each of the struts is a substantially straight member such that the entirety of the struts and the nodes of the triangular truss units lie in substantially the same plane is referred to as a "planar triangular truss unit." As used herein a "triangular space truss" is a space truss including one or more triangular truss units.

In various embodiments, the trusses 102 of the web structure may include one or more planar truss units (e.g., planar triangular truss units) constructed with straight or curved/arched members (e.g., struts) connected at various nodes. In some embodiments, the trusses 102 may be micro-trusses. A "micro-truss" is a truss having dimensions sufficiently small enough such that a plurality of micro-trusses can be assembled or other wise coupled to one another to form a web structure having a small enough overall dimension (e.g., height, length and width) such that substantially all of the web structure can be inserted into an implant location (e.g., between two vertebra). Such a web structure and its micro-trusses can thus be employed to receive and distribute throughout the web structure loading forces of the surrounding tissue (e.g., vertebra, bone, or the like). In one embodiment, the diameters of the struts forming the micro-truss may be between about 0.25 millimeters (mm) and 5 mm in diameter (e.g., a diameter of about 0.25 mm, 0.5 mm, 0.6 mm, 0.7 mm, 0.8 mm, 0.9 mm, 1 mm, 2 mm, 3 mm, 4 mm, or 5 mm). In one embodiment, a micro-truss may have an overall length or width of less than about 1 inch (e.g., a length less than about 0.9 in, 0.8 in, 0.7 in, 0.6 in, 0.5 in, 0.4 in, 0.3 in, 0.2 in, 0.1 in).

As depicted, for example, in FIGS. 1A-1B, the web structure may extend throughout implant 100 (including the central portion of implant 100) to provide support throughout implant 100. Trusses 102 of implant 100 may thus support implant 100 against tensile, compressive, and shear forces. Web structure may also reinforce implant 100 along multiple planes. The external truss structure may, for example, provide support against tensile and compressive forces acting vertically through the implant, and the internal web structure may provide support against tensile, compressive, and shear forces along the various planes containing the respective trusses. In some embodiments, the web structure includes trusses 102 that form a triangulated web structure with multiple struts (e.g., struts 103a-f) (struts are generally referred to herein as "struts 103").

In one embodiment, web structure of the implant 100 may include an internal web structure that is at least partially enclosed by an external truss structure. For example, in one embodiment, web structure 101 may include an internal web structure that includes a space truss having at least a portion of the space truss surrounded by an external truss structure that includes one or more planar trusses formed with a plurality of planar truss units that lie substantially in a single plane. FIG. 1A depicts an embodiment of implant 100 having an internal web structure 104 and an external truss structure 105. In the illustrated embodiment, internal web structure 104 includes a space truss defined by a plurality of planar truss units 106 coupled at an angle with respect to one another such that each adjacent truss unit is not co-planar with each adjacent truss units. Adjacent truss units may include two truss units that share a strut and the respective two nodes at the ends of the shared strut.

In one embodiment, external truss structure 105 includes a plurality of planar trusses that are coupled about an exterior, interior or other portion of the implant. For example, in the illustrated embodiment, the external truss structure 105 includes a series of planar trusses 107a,b that are coupled to one another. Planar truss 107a is denoted by a dashed line [ - - - - - ], planar truss 107b is denoted by dotted-dashed line [- • - • -]. Each planar truss is formed from a plurality of planar truss units (e.g., triangular planar truss units. As depicted, planar truss 107a includes four triangular planar truss units 108a,b,c,d having a common vertex 110 and arranged to form a generally rectangular structure that lies in a single common plane. In other words, the four triangular planar truss units are arranged to form a substantially rectangular structure having "X" shaped struts extend from one corner of the rectangular structure to the opposite corner of the rectangular structure. As depicted, the substantially rectangular structure may include a trapezoidal shape. As described in more detail below, the trapezoidal shape may be conducive to providing an implant including lordosis. Lordosis may include an angled orientation of surfaces (e.g., top and bottom) of an implant that provides for differences in thickness in anterior and posterior regions of the implant such that the implant is conducive for supporting the curvature of a vertebral column.

In one embodiment, the planar trusses that form the external truss are coupled to one another, and are aligned along at least one axis. For example, in FIG. 1A, planar truss section 107a is coupled to an adjacent planar truss 107b. Planer truss sections 107a,b are not parallel in all directions. Planar truss sections 107a,b are, however, arranged parallel to one another in at least one direction (e.g., the vertical direction between the top and the bottom faces of implant 100). For example, planar trusses 107a,b and the additional planar trusses are arranged in series with an angle relative to one another to form a generally circular or polygon shaped enclosure having substantially vertical walls defined by the planar trusses and the planar truss units arranged in the vertical direction.

Figure 2A:
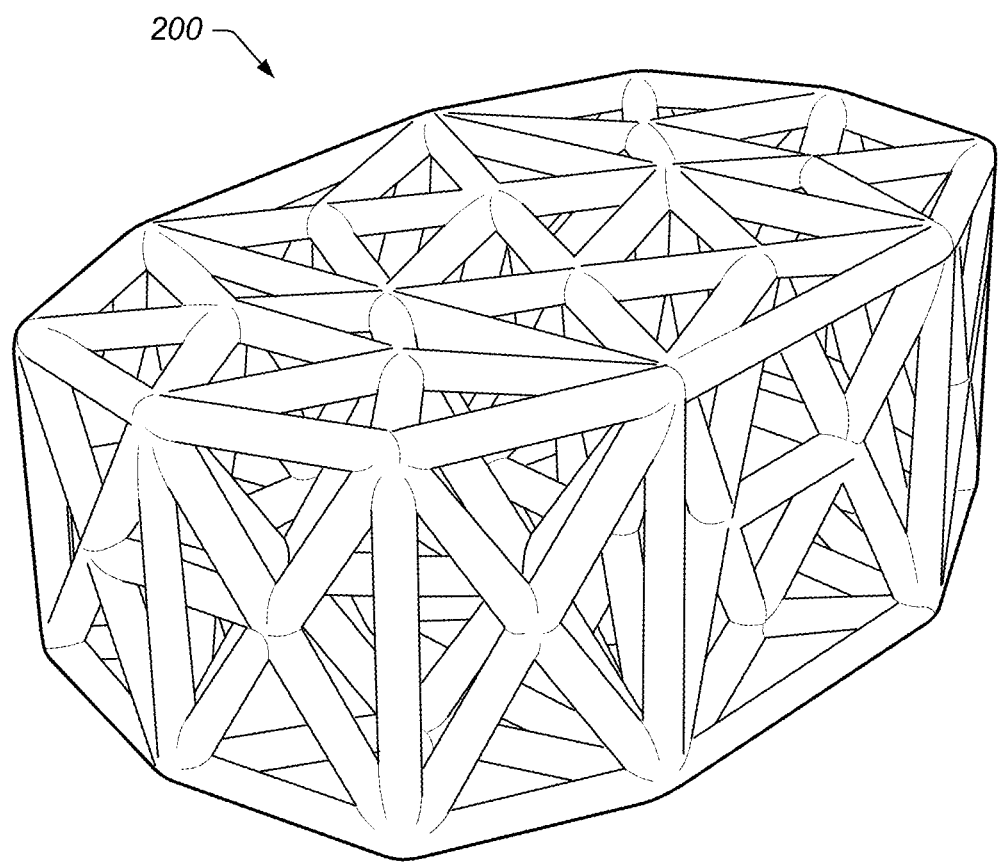
FIGS. 2A-2D illustrate views of an implant without lordosis, according to an embodiment.
Figure 2B:
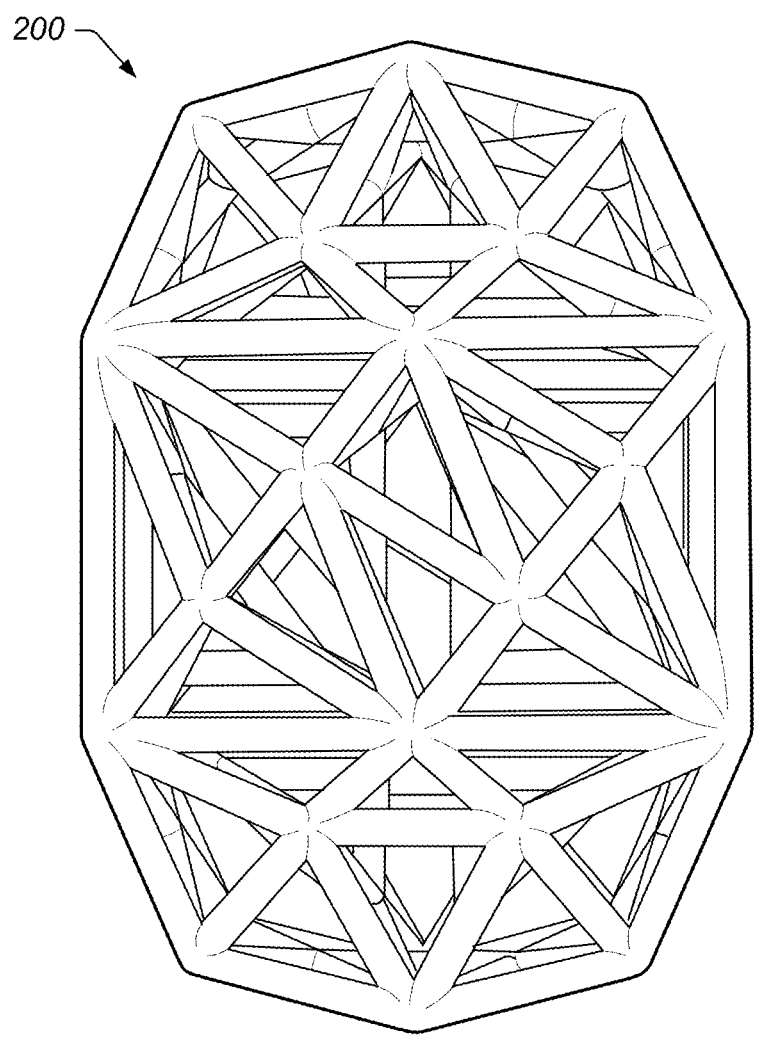
Figure 2C:
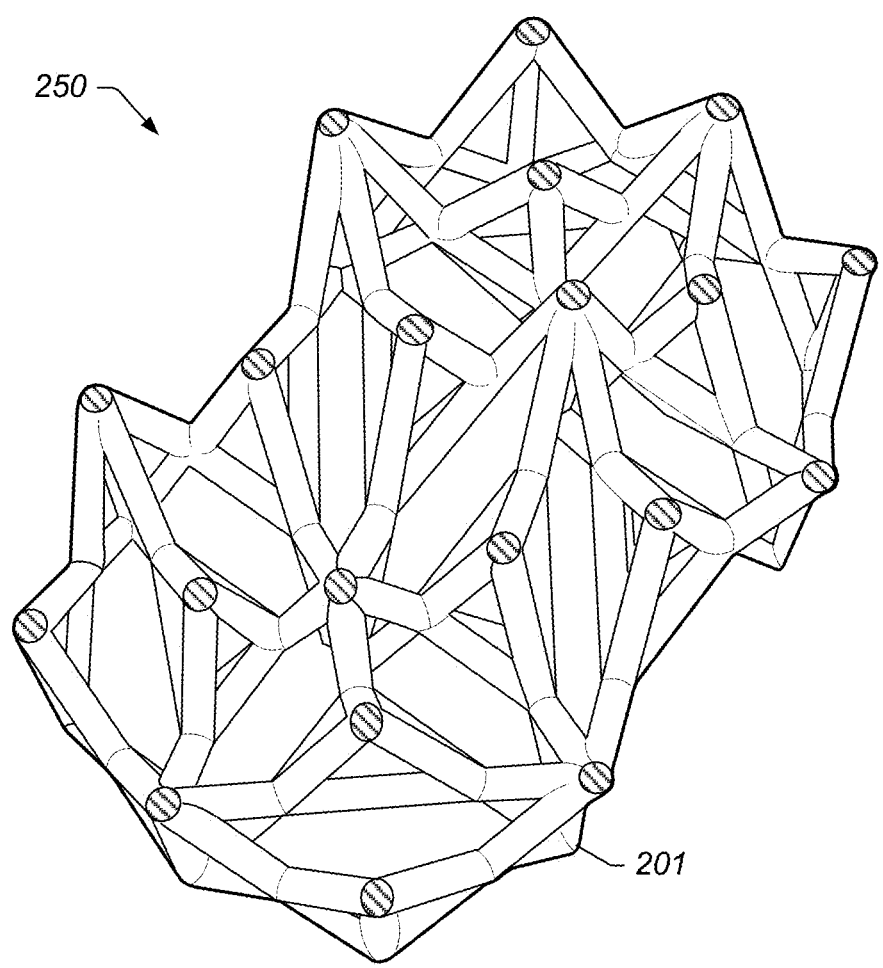

In one embodiment, the external truss portion may encompass the sides, top, and/or bottom of the implant. For example, in one embodiment, the external truss portion may include a top region, side regions, and/or a bottom region. FIG. 1A depicts an embodiment of implant 100 wherein external truss portion 105 includes a top 111, bottom 112 and a side region 113. As described above, side region 113 includes a series of planar trusses arranged vertically to form a circular/polygon ring-like structure that completely or at least partially surrounds the perimeter of the space truss disposed in the central portion of implant 100. In the depicted embodiment, top portion 111 of external truss structure 105 includes a plurality of truss units coupled to one another to form a planar truss that cover substantially all of the top region of internal web structure 104. In the illustrated embodiment, the top portion 111 spans entirely the region between top edges of the side portion 113 of external truss structure 105. In the illustrated embodiment, top portion 111 is formed from a single planar truss that includes a plurality of truss units that lie in substantially the same plane. In other words, the planar truss of top portion 111 defines a generally flat surface. Although difficult to view in FIG. 1, the underside of implant 100 may include the bottom portion 112 having a configuration similar to that of the top portion 111. In other embodiments, external truss structure 105 may include a partial side, top and/or bottom external truss portions. Or may not include one or more of the side, top and bottom external truss portions. For example, as described in more detail below, FIG. 2C depicts an embodiment of implant 100 that includes an internal web structure formed from space trusses, that does not have an external truss structure.

In some embodiments, implant 100 may be formed from a biocompatible material such as a titanium alloy (e.g., γTitanium Aluminides), cobalt, chromium, stainless steel, Polyetheretherketone (PEEK), ceramics, etc. Other materials are also contemplated. In some embodiments, implant 100 may be made through a rapid prototyping process (e.g., electron beam melting (EBM) process) as further described below. Other processes are also possible (e.g., injection molding, casting, sintering, selective laser sintering (SLS), Direct Metal Laser Sintering (DMLS), etc). SLS may include laser-sintering of high-performance polymers such as that provided by EOS of North America, Inc., headquartered in Novi, Mich., U.S.A. High-performance polymers may include various forms of PEEK (e.g., HP3 having a tensile strength of up to about 95 mega Pascal (MPa) and a Young's modulus of up to about 4400 MPa and continuous operating temperature between about 180° C. (356° F.) and 260° C. (500° F.)). Other materials may include PA 12 and PA 11 provided by EOS of North America, Inc.

Figure 7:
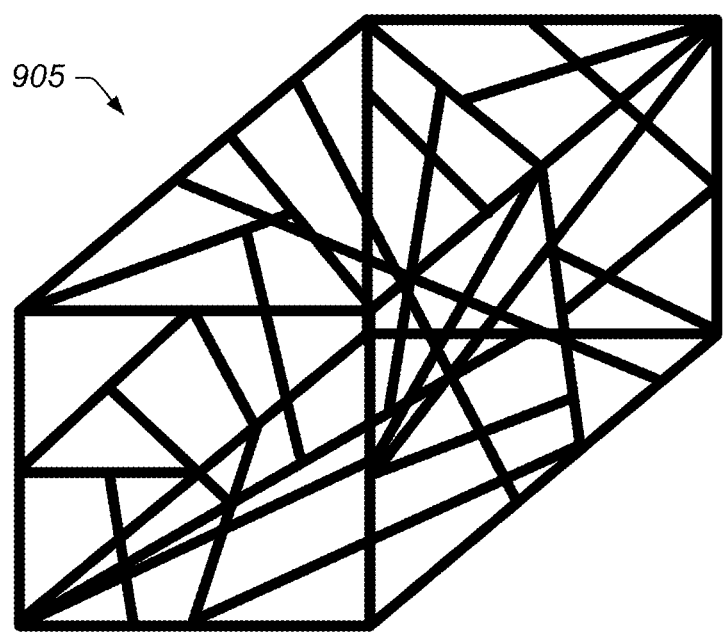
FIG. 7 illustrates a random web structure, according to an embodiment.

As described above, in some embodiments the web structure may be formed from a plurality of triangular planar truss units. In some embodiments, the planar truss units may be coupled to each other to define polyhedrons that define the internal web structure. Examples of polyhedron structures that may be created by joining planar truss units include, but are not limited to, tetrahedrons, pentahedrons, hexahedrons, heptahedrons, pyramids, octahedrons, dodecahedrons, icosahedrons, and spherical fullerenes. In some embodiments, such as those described above, the space truss of the web structure may connect multiple midpoints of tetrahedron building blocks and include a regular pattern of tetrahedron blocks arranged adjacent one another. In some embodiments, the web structure may not include a pattern of geometrical building blocks. For example, FIG. 7 illustrates an irregular pattern of struts that may be used in an implant 905. Other web structures are also contemplated. Examples of implants composed of a web structure are described in U.S. Published Patent Applications Nos.: 2010/0161061; 2011/0196495; 20110313532; and 2013/0030529, each of which is incorporated herein by reference.

Figure 3A:
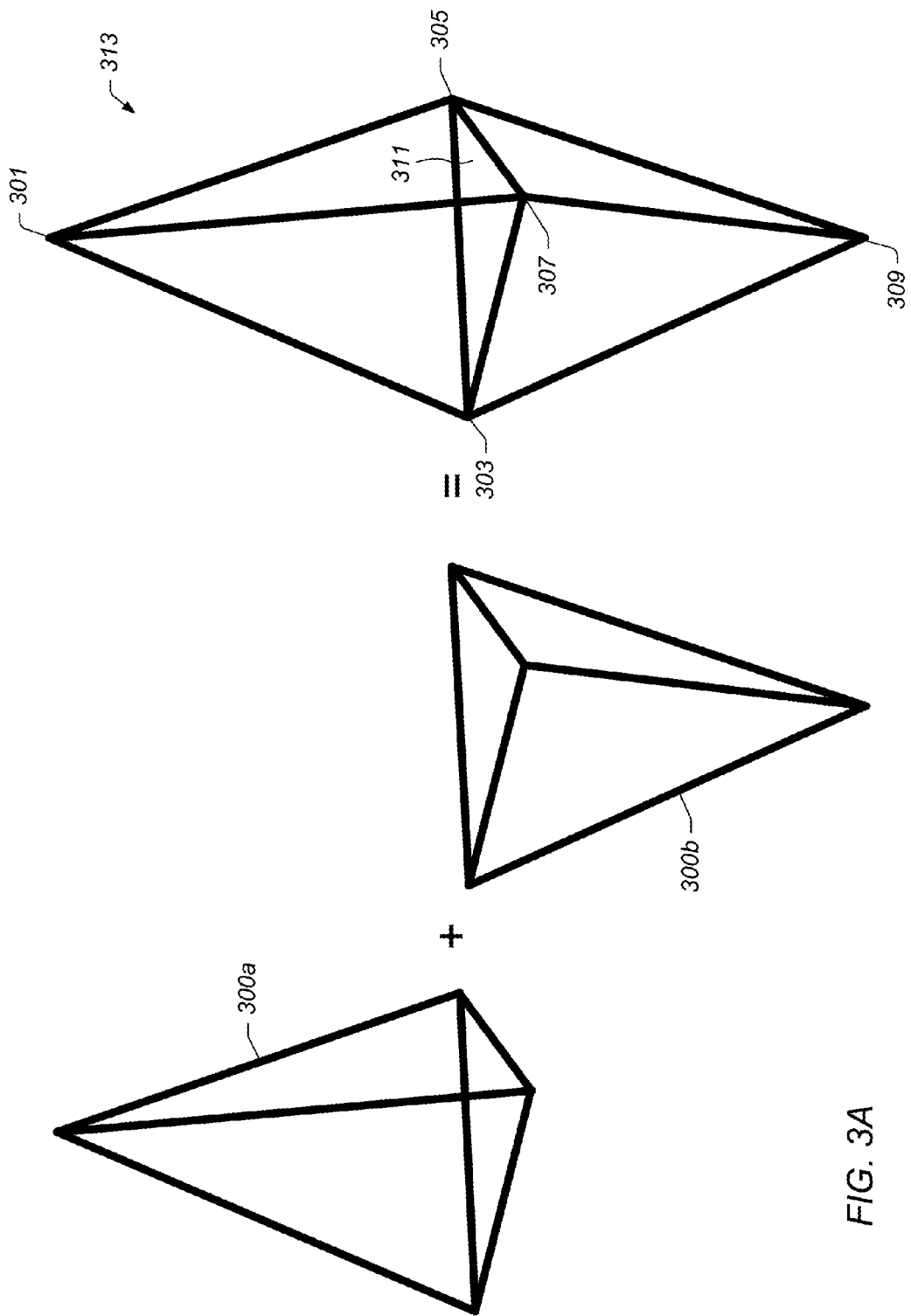
FIGS. 3A-3B illustrate a web structure formed with triangular-shaped building blocks, according to an embodiment.
Figure 3B:
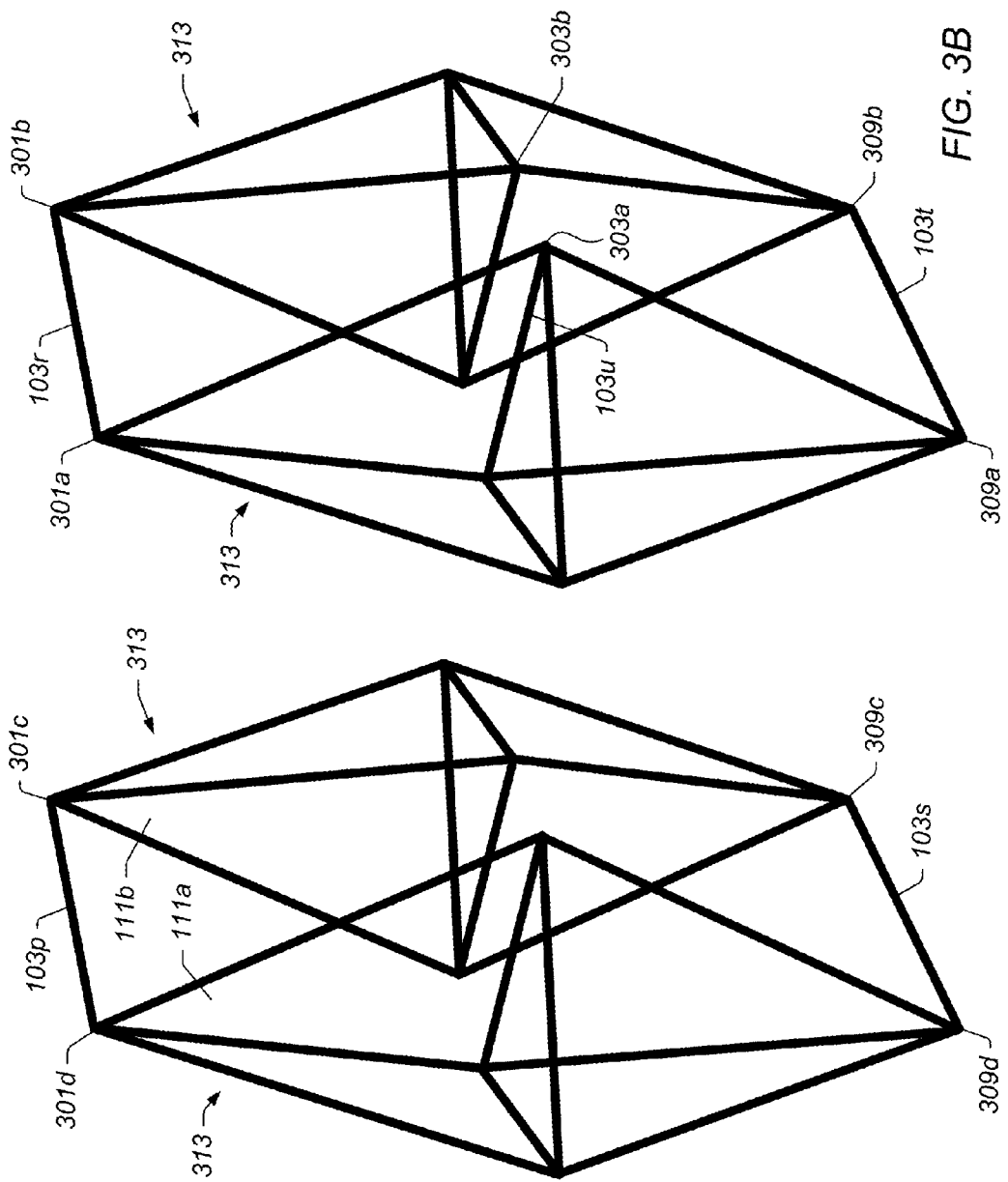

FIGS. 3A-3B illustrate a schematic view of a portion of an internal web structure formed with space units formed from triangular planar truss units. Triangular planar truss units may be joined together to form tetrahedrons 300a,b that may also be used as building blocks (other patterns from the triangles are also contemplated). Other building blocks are also contemplated (e.g., square-shaped building blocks). In some embodiments, a web structure may include a single tetrahedron, such as tetrahedron 300a or 300b alone or in combination with one or more other polyhedron. In some embodiments, a web structure may include two or more tetrahedrons 300a,b. Tetrahedron 300a may include four triangular faces in which three of the four triangles meet at each vertex. In some embodiments, two tetrahedrons 300a and 300b may be placed together at two adjacent faces to form space truss 313 with a hexahedron-shaped frame (including six faces). Hexahedron-shaped space truss 313 may include first vertex 301, second vertex 309, third vertex 303, fourth vertex 305, and fifth vertex 307. Common plane 311 may be shared by two tetrahedrons (e.g., common plane 311 may include third vertex 303, fourth vertex 305, and fifth vertex 307) to form a hexahedron with first vertex 301 and second vertex 309 spaced away from common plane 311. As depicted, the center portion of the triangular shaped building blocks may have a void region in their center that does not include any additional members (e.g., no members other than the struts forming the triangular shaped building blocks) extending there through.

As seen in FIG. 3B, in some embodiments, multiple hexahedron-shaped space trusses 313 may be arranged in a side-by-side manner. Two space trusses 313 of implant 100 may be connected via their first vertices 301a,b through strut 103r and connected via their second vertices 309a,b through strut 103t. Similarly, two space trusses 313 may be connected via their first vertices 301c,d through strut 103p and connected via their second vertices 309c,d through strut 103s. Other connections are also possible. For example, space trusses 313 may connect directly through side vertices (e.g., directly through corresponding vertices (such as vertices 303a,b) and/or share a common strut (such as strut 103u)) and/or through a side face (e.g., side faces 111a,b).

Figure 4A:
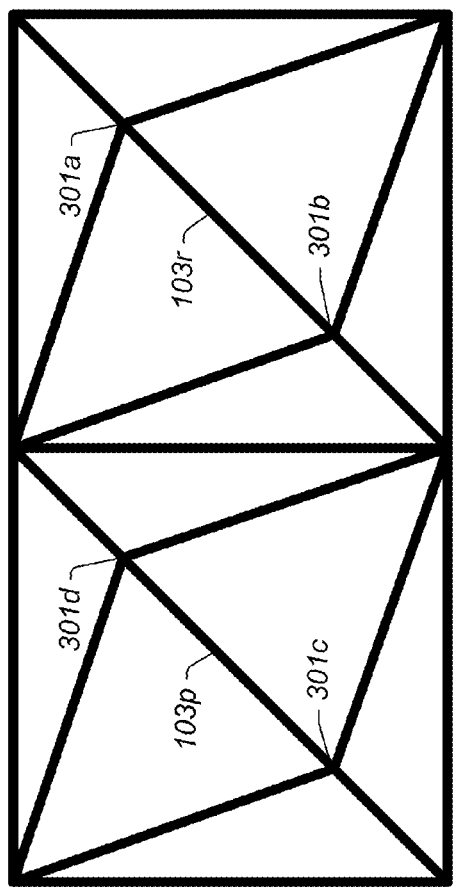
FIGS. 4A-4B illustrate a top structure of an internal web structure of the implant, according to an embodiment.
Figure 4B:
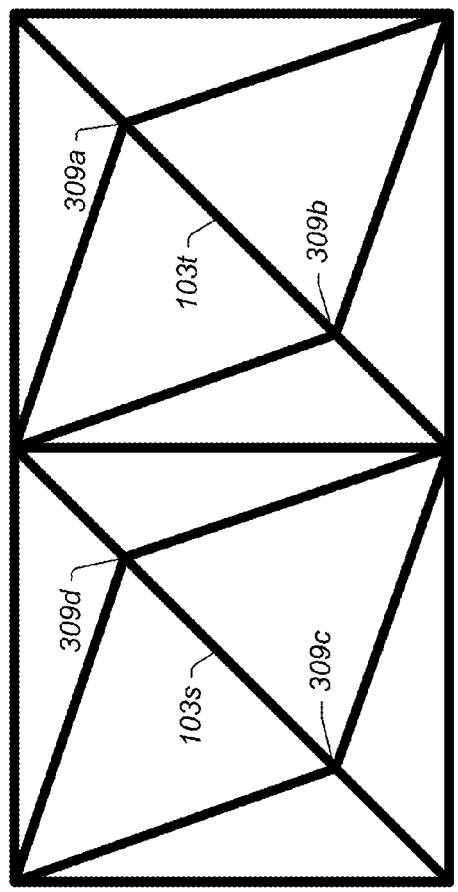

FIG. 4A illustrates additional struts 103 (e.g., struts 103p and 103r) connecting the first vertices (represented respectively by 301a, 301b, 301c, and 301d) of four hexahedron-shaped space trusses in implant 100. FIG. 4B illustrates additional struts 103 (e.g., struts 103s and 103t) connecting second vertices 309 (represented respectively by 309a, 309b, 309c, and 309d) of four hexahedron-shaped space trusses in implant 100. In some embodiments, additional struts 103 may also be used internally between one or more vertices of the web structures to form additional trusses (e.g., see web structures in FIGS. 1A-2B) (other structures are also possible).

As shown in FIG. 1A, top surface 115a and bottom surface 115b of implant 100 may include triangles, squares, circles or other shapes (e.g., a random or custom design). Top and bottom surfaces 115a,b may be used to connect the top and bottom vertices of various geometrical building blocks used in the web structure of implant 100. For example, each vertex may be connected through struts to the neighboring vertices of other geometrical building blocks. Top surface 115a may include other strut networks and/or connections. In some embodiments, bottom surface 115b may mirror the top surface (and/or have other designs). In some embodiments, top surface 115a and bottom surface 115b may engage respective surfaces of two adjacent vertebrae when implant 100 is implanted.

As depicted in FIG. 1B, implant 100 may include lordosis (e.g., an angle in top and/or bottom surfaces 115a,b approximately in a range of 4 to 15 degrees (such as 4, 5, 6, 7, 8, 9, 10, 11, 12, 13, 14, or 15 degrees)) to further support the adjacent vertebrae when implanted. As described above, lordosis may include an angled orientation of surfaces (e.g., top and bottom) that provide for differences in thickness in the anterior and posterior portions of the implant such that the implant is conducive for supporting the curvature of a vertebral column. In the illustrated embodiment, the thickness of implant 100 is greater at or near the anterior portion 118 and lesser at or near the posterior portion 120 of the implant. In the illustrated embodiment, the side portions of external truss structure are arranged substantially vertically, and the lordosis is formed by the angles of the top portion 111 and bottom portion 112 of external truss structure. For example, in the illustrated embodiment, top portion 111 and bottom portion 112 of external truss structure are not perpendicular to the vertical plane defined by the side portion 113. Rather, the top portion 111 and bottom portion 112 are arranged with an acute angle relative to the vertical plane of side portion 113 at or near the anterior region 118 of implant 100 and with an obtuse angle relative to the vertical plane of side portion 113 at or near posterior region 120 of implant 100. As depicted, the vertical struts that form the planar truss of side portion 113 of external truss structure proximate posterior region 120 of implant 100 are shorter than struts that form side portion of external truss structure proximate anterior region 118 of implant 100. In the illustrated embodiment, in which the vertical trusses are substantially evenly spaced, the struts forming the "X" cross members of the side planar trusses proximate the posterior region 120 of implant 100 are shorter than struts forming the "X" cross members of the side planar trusses proximate the anterior region 118 of implant 100. Other embodiments may include variations in the arrangement of the trusses to provide various configurations of the implant. For example, in some embodiments only one or neither of the top and bottom external truss portions may be non-perpendicular to the side portions of the external truss proximate the anterior and posterior portions of the implant. Further, the side, top, and/or bottom portions may include multiple planar trusses angled relative to one another in any orientation. For example, the top or bottom portions may include four planar trusses, each formed of multiple truss units, such that the portion(s) includes a pyramidal like shape.

Figure 2D:
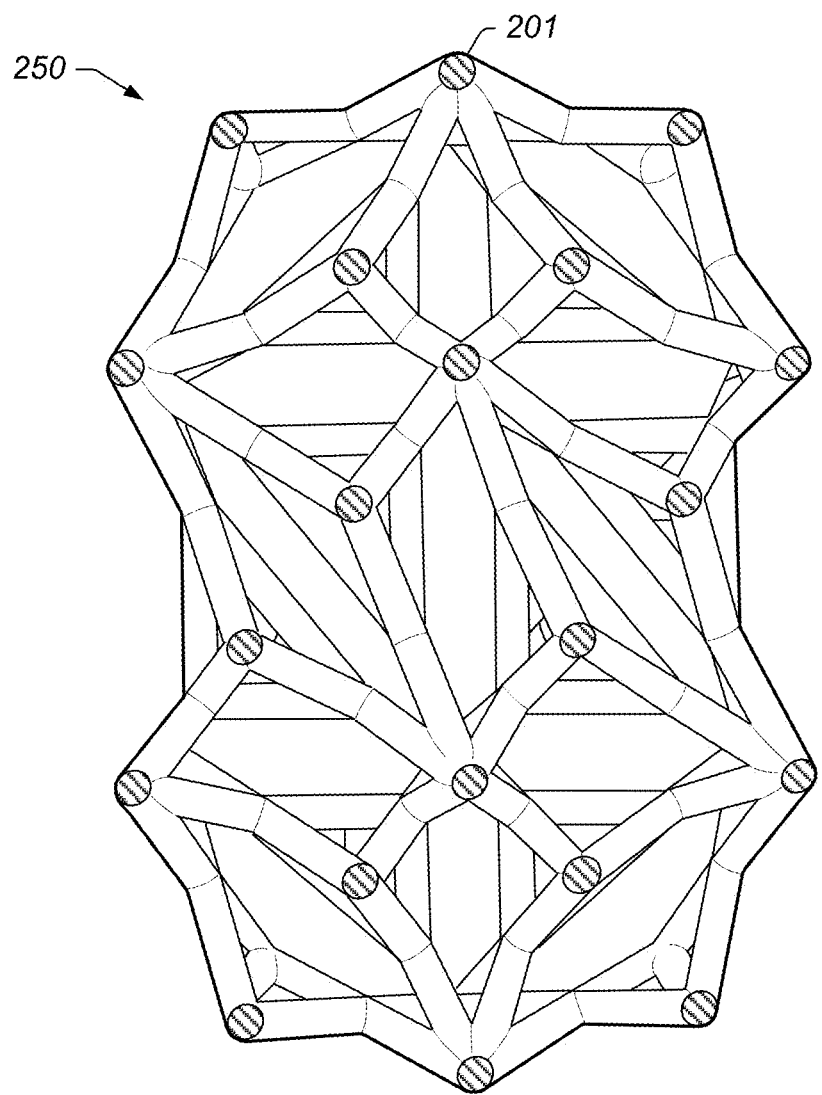

In some embodiments, the implant may not include lordosis. For example, FIGS. 2A-2B illustrate two views of an embodiment of an implant 200 without lordosis. In some embodiments, the top surface and bottom surface may not include connecting struts. For example, FIGS. 2C-2D illustrate two views of implant 250 without outer struts (e.g., without external truss portions formed of planar trusses). In the illustrated embodiment, implant 250 includes an internal web structure and does not include an external truss structure. For example, in the illustrated embodiment, the exterior faces of implant 250 are defined by a plurality of truss units that are angled relative to each of its adjacent truss units. The relative alignment of the truss units results in a non-planar exterior that includes a plurality of pointed junctions. The pointed junctions (e.g., pointed junction 201) may operate to dig into the surrounding bone to hold the implant in place (for example, if the implant is being used in a corpectomy device).

Figure 5A:
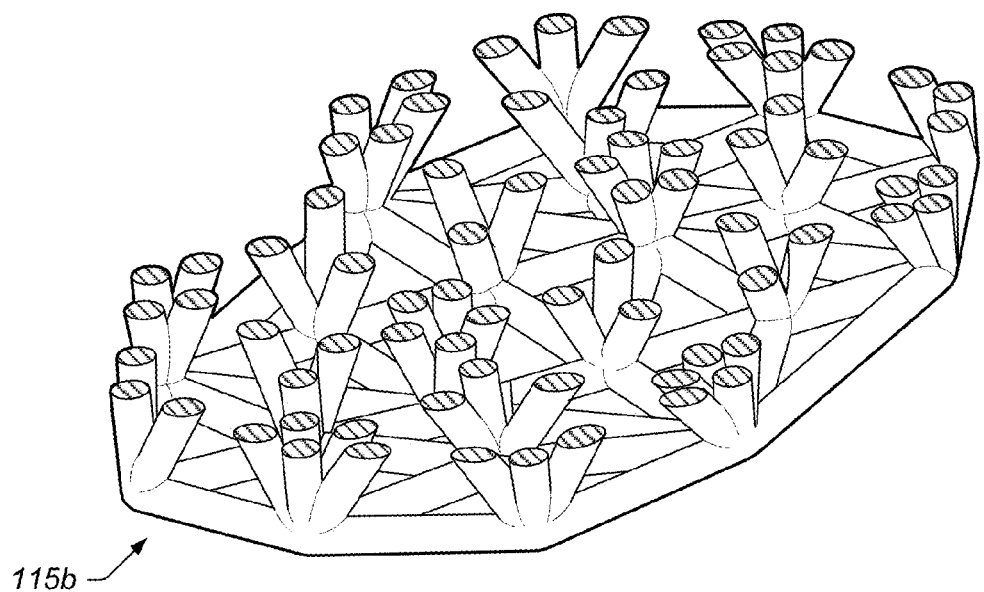
FIGS. 5A-5C illustrate progressive sectioned views of the implant showing the internal structure of the implant, according to an embodiment.
Figure 5B:
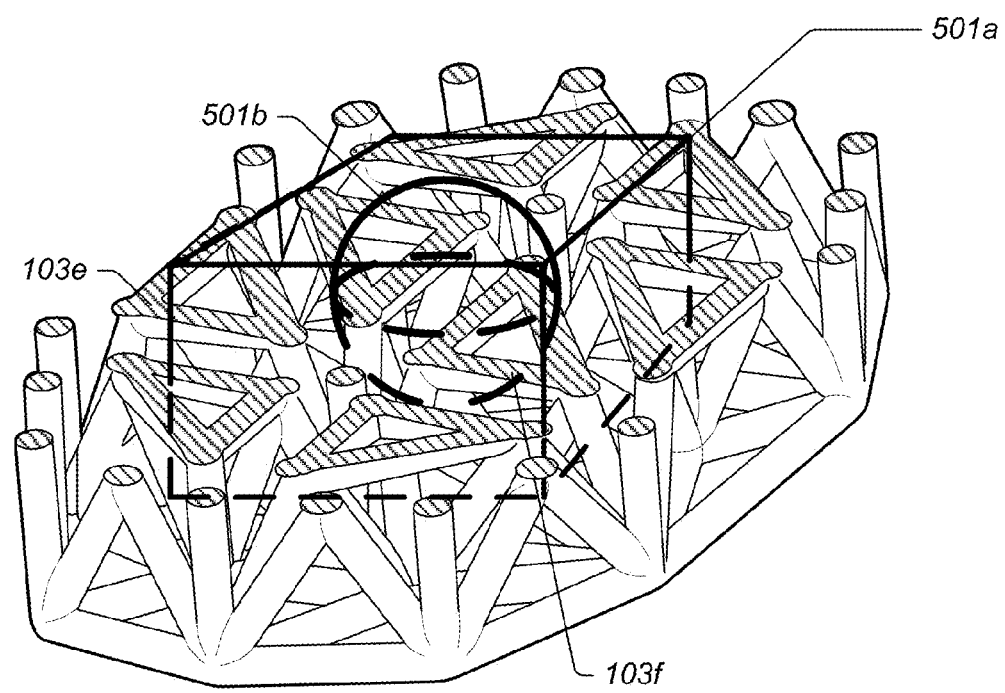
Figure 5C:
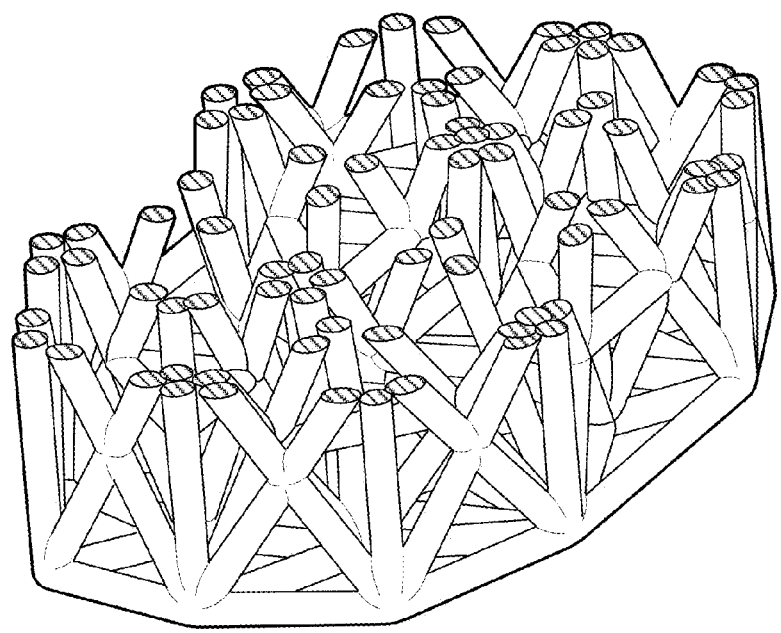
Figure 5D:
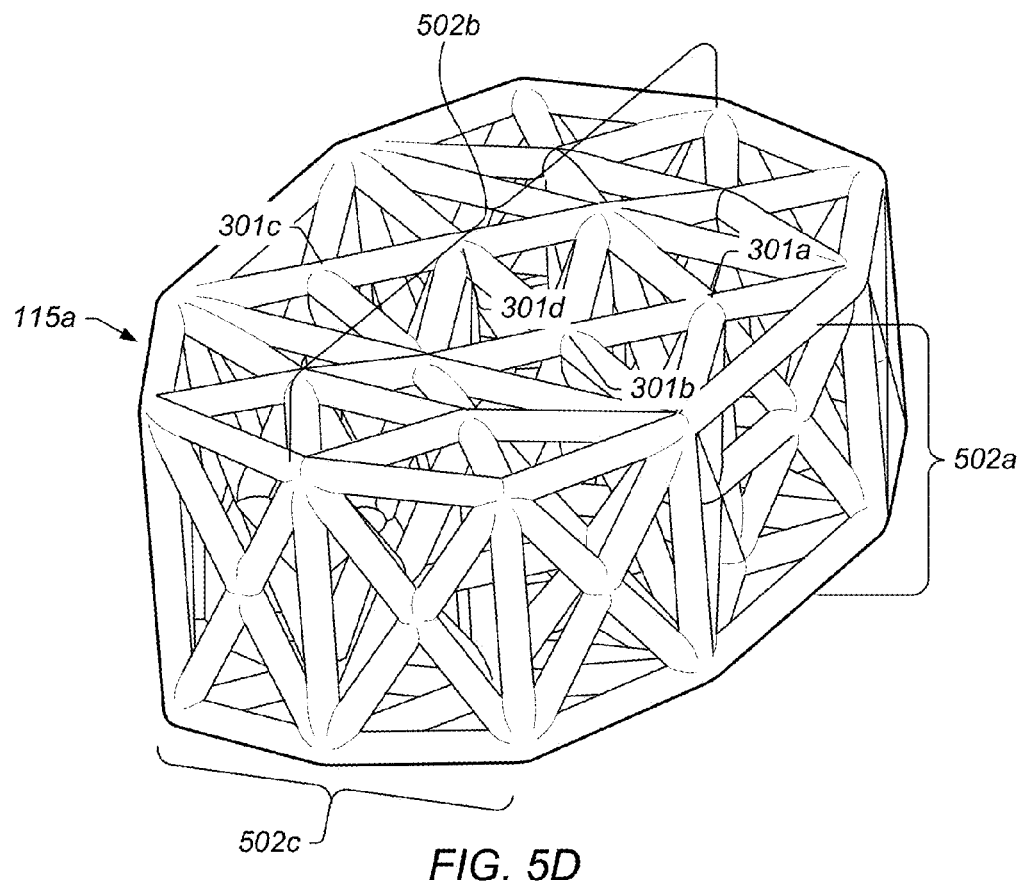
FIG. 5D illustrates an isometric view of the implant, according to an embodiment.

FIGS. 5A-5C illustrate progressive sectioned views of implant 100 showing the internal structure of implant 100, according to an embodiment. FIG. 5A illustrates a sectioned view of a lower portion of implant 100. Bottom surface 115b is shown with various struts (e.g., struts 103) extending upward from bottom surface 115b. FIG. 5B illustrates a sectioned view approximately mid-way through implant 100. Struts, such as struts 103e,f, shared by various stacked tetrahedrons in the web structure are shown. Some struts extend through central portion 501a and/or 501b of implant 100. FIG. 5B also shows central portions 501a,b of implant 100. In some embodiments, central portion 501a may include a rectangular region that has a width of approximately 50% of the implant width, a height of approximately 50% of the implant height, and a length of approximately 50% of the implant length and located in the center of implant 100. In some embodiments, central portion 501b may encompass a region (e.g., a spherical region, square region, etc.) of approximately a radius of approximately ⅛ to ¼ of the width of implant 100 around a position located approximately at one half the width, approximately one half the length, and approximately one-half the height of implant 100 (i.e., the center of implant 100). Other central portions are also contemplated. For example, the central portion may include a square region with a length of one of the sides of the square region approximately ¼ to ½ the width of implant 100 around a position approximately at one half the width, approximately one half the length, and approximately one half the height of the implant. An example height 502a, width 502b, and length 502c, is shown in FIG. 5D. In some embodiments, the height may be up to about 75 mm or more. In some embodiments, such as those used for long bone reconstruction, the width and/or length could be approximately 7 inches or longer. In some embodiments, the width, length, and/or height may vary along implant 100 (e.g., the height may vary if the implant includes lordosis). The height may be taken at one of the opposing sides, the middle, and/or may be an average of one or more heights along the length of implant 100. The web structure may extend through central portion 501a,b of the implant (e.g., at least one strut of the web structure may pass at least partially through central portion 501a,b). FIG. 5C illustrates another sectioned view showing sectioned views of top tetrahedrons in the web structure. FIG. 5D shows a complete view of implant 100 including top surface 115a with vertices 301a-d.

Figure 6A:
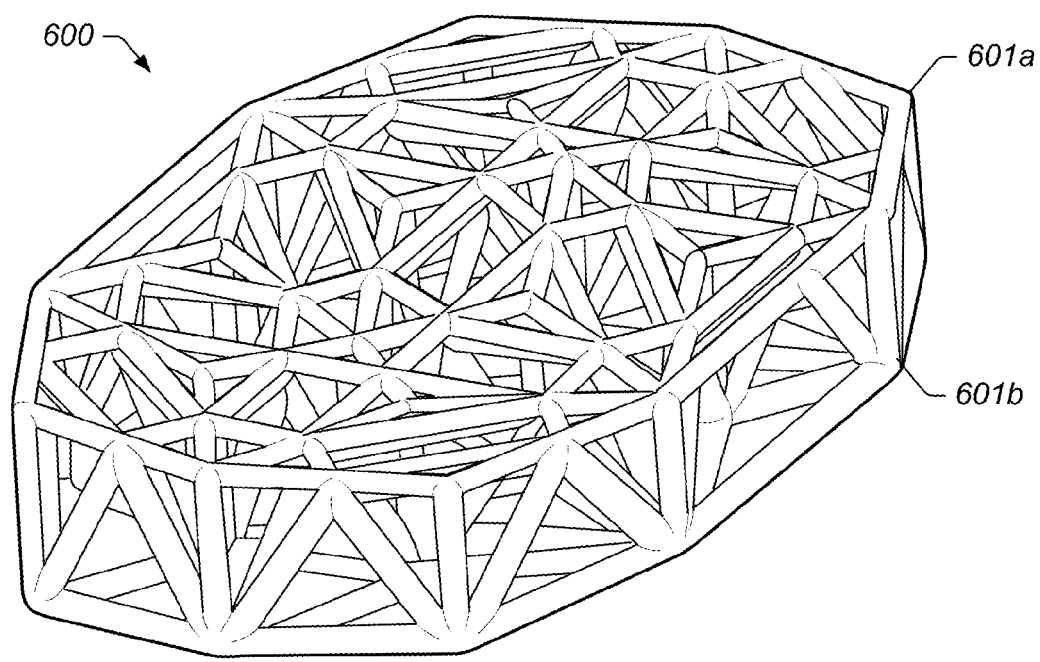
FIGS. 6A-6D illustrate another configuration of the web structure, according to an embodiment.
Figure 6B:
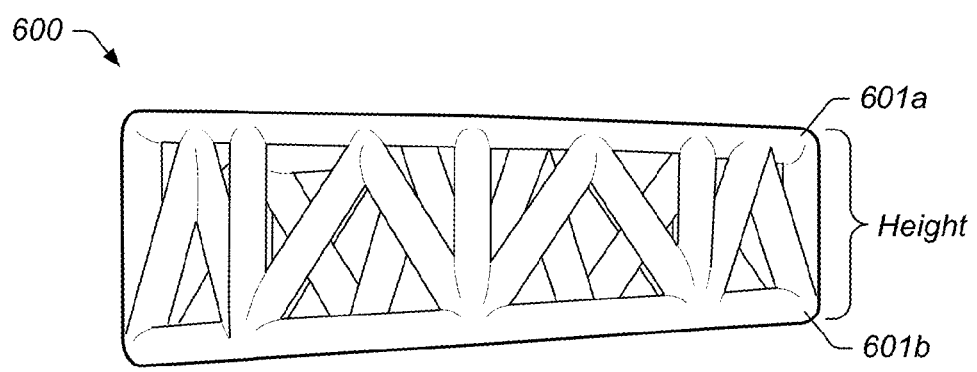

FIGS. 6A-6D illustrate alternate embodiments of an implant. In some embodiments, different sections of the hexahedron-shaped geometric design may be used. For example, as seen in FIG. 6A, the bottom half of the hexahedron-shaped geometric design may be used (primarily including the lower tetrahedron structures). If using the bottom half of the design, implant 600 may be expanded proportionately to have similar overall dimensions as the hexahedron-shaped geometric design (e.g., the tetrahedrons may be expanded to approximately twice the height of the tetrahedrons in the hexahedron-shaped geometric design to give implant 600 a height approximately the same as the hexahedron-shaped geometric design). In some embodiments, implant 600 may also be angled (e.g., on top surface 601a and/or bottom surface 601b) to provide implant 600 with lordosis to, in some embodiments, have a better fit between the vertebral endplates. Top surface 601a and/or bottom surface 601b may also include struts to connect nodes of implant 600 (e.g., see the strut network on the top surface in FIG. 6a). Other patterns of struts for top surface 601a and/or bottom surface 601b may also be used. In some embodiments, implant 600 may not include negative angles between struts and may thus be easier to create through a casting or molding process.

Figure 6C:
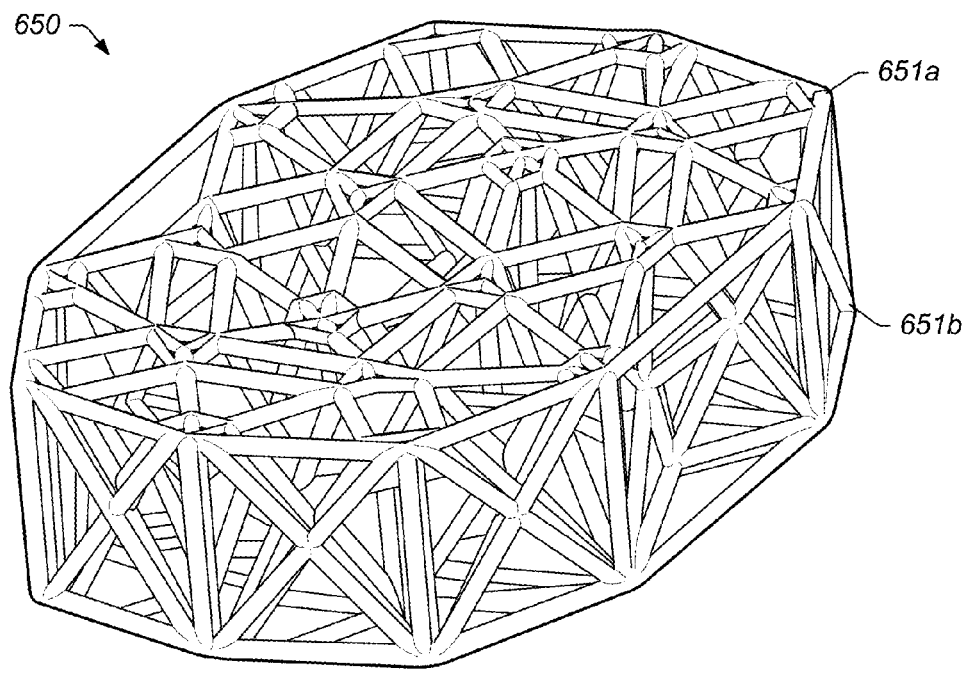
Figure 6D:
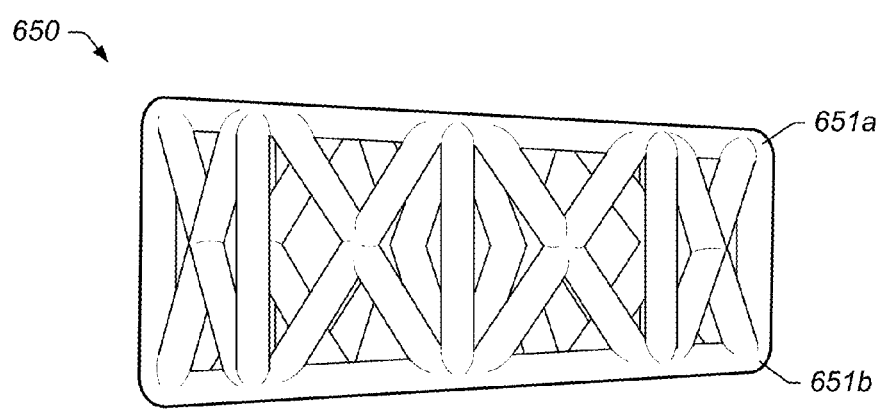

FIGS. 6C-6D illustrate another alternate embodiment of an implant. In some embodiments, approximately the middle 40 to 60 percent of the hexahedron-shaped geometric design may be used in implant 650. For example, if an overall height of the hexahedron-shaped geometric design is approximately 37 mm, approximately the bottom 10 mm and approximately the top 10 mm of the design may be removed and approximately the middle 17 mm of the design may be used for the implant. Middle portion of implant 650 may then be expanded proportionately such that the approximate height of the expanded design may be approximately 37 mm (or a different height as needed). Top surface 651a and bottom surface 651b may include a network of struts (e.g., see the struts on top surface 651a of FIG. 6C) (other networks of struts are also contemplated). Other portions of the design for the implant are also contemplated (e.g., the top half of the design shown in FIG. 1A, the bottom half of the design shown in FIG. 1A, etc). Design portions may be proportionately expanded to meet specified dimensions (e.g., specified height, width, and length). In some embodiments, the amount of struts may be reduced or material in the implant may be redistributed so that some struts may have a larger diameter and some may have a smaller diameter (e.g., the different diameters may reinforce against different directional forces). In some embodiments, a partial-design cage may be used (e.g., with half of the web structure so that the structure includes a tetrahedron. Further, in some embodiments, the implant may include angled surfaces (e.g., an angled top surface 651a and/or angled bottom surface 651b) to provide lordosis for implants to be implanted between the vertebral endplates.

In some embodiments, the web structure of an implant may distribute forces throughout the implant when implanted. For example, the connecting struts of the web structure may extend throughout the core of an implant, and the interconnectivity of struts may disperse the stress of compressive forces throughout implant to reduce the potential of stress risers (the distribution of forces throughout the implant may prevent concentration of stress on one or more portions of the vertebrae that may otherwise result in damage to the vertebrae).

In some embodiments, the web structure of an implant (e.g., the external and internal struts of the implant) may also provide surface area for bone graft fusion. For example, the web structure extending throughout an implant may add additional surface areas (e.g., on the surface of the struts making up the implant) to fuse to the bone graft material and prevent bone graft material from loosening or migrating from the implant. In some embodiments, the web structure may also support bone in-growth. For example, when implanted, adjacent bone (e.g., adjacent vertebrae if the implant is used as a spinal implant) may grow over at least a portion of struts of the implant. The bone growth and engagement between the bone growth and the implant may further stabilize the implant. In some embodiments, the surfaces of the implant may be formed with a rough surface to assist in bone in-growth adhesion.

In some embodiments, struts may have a diameter approximately in a range of about 0.025 to 5 millimeters (mm) (e.g., 1.0 mm, 1.5 mm, 3 mm, etc). Other diameters are also contemplated (e.g., greater than 5 mm). In some embodiments, the struts may have a length approximately in a range of 0.5 to 20 mm (e.g., depending on the implant size needed to, for example, fit a gap between vertebral endplates). As another example, struts may have a length approximately in a range of 30-40 mm for a hip implant. In some embodiments, the reduced strut size of the web structure may allow the open cells in implant 100 to facilitate bone growth (e.g., bone may grow through the open cells once implant 100 is implanted in the body). Average subsidence for implants may be approximately 1.5 mm within the first 3 weeks post op (other subsidence is also possible (e.g., approximately between 0.5 to 2.5 mm)). A strut size that approximately matches the subsidence (e.g., a strut size of approximately 1.5 mm in diameter and a subsidence of approximately 1.5 mm) may result in a net 0 impedance (e.g., the bone growth growing around the struts) after the implant has settled in the implanted position. The net 0 impedance throughout the entire surface area of the implant/ vertebrae endplate interface may result in a larger fusion column of bone that may result in more stable fusion. Other fusion column sizes are also contemplated. The configuration of the implant may redistribute the metal throughout the implant. In some embodiments, a rim may not be included on the implant (in some embodiments, a rim may be included). The resulting bone growth (e.g., spinal column) may grow through the implant.

In some embodiments, greater than 50% of the interior volume of implant 100 may be open. In some embodiments, greater than 60%, greater than 70%, and/or greater than 80% of implant 100 may be open (e.g., 95%). In some embodiments, the open volume may be filled with bone growth material. For example, cancellous bone may be packed into an open/internal region of implant.

In some embodiments, at least a portion of the surfaces of the implant may be coated/treated with a material intend to promote bone growth and/or bone adhesion and/or an anitmicrobial agent to prevent infections. For example, in some embodiments, the surface of the struts may be coated with a biologic and/or a bone growth factor. In some embodiments, a biologic may include a coating, such as hydroxyapatite, bone morphaginic protein (BMP), insulinlike growth factors I and II, transforming growth factor-beta, acidic and basic fibroblast growth factor, platelet-derived growth factor, and/or similar bone growth stimulant that facilitates good biological fixation between the bone growth and a surface of the implant. In some embodiments, a bone growth factor may include a naturally occurring substance capable of stimulating cellular growth, proliferation and cellular differentiation (e.g., a protein or steroid hormone). In some embodiments, the surface of the implant (e.g., the struts, the external truss structure, etc.) may be coated with collagen.

In some embodiments, a biologic and/or growth factor may be secured to a central region of an implant. For example, in some embodiments, a biologic or growth factor may be provided on at least a portion of a strut that extends through central portion 501*a* and/or 501*b* of implant 100, see FIG. 5B. Such an embodiment may enable the delivery of a biologic and or a growth factor to a central portion of an implant. For example, the biologic or growth factor may be physically secured to a strut in a central portion of the implant as opposed to being packed into an open volume that does not include a strut provided therein for the physical attachment of the biologic and/or growth factor.

As the implant settles into the implant site, subsidence may place additional pressure on the bone graft material (which may already be under compressive forces in the implant) and act to push the bone graft material toward the sides of the implant (according to Boussinesq's theory of adjacent material, when a force is applied to a member that is adjacent to other materials (such as sand, dirt, or bone graft material) the force against the member creates a zone of increased pressure (e.g., 60 degrees) in the adjacent material). Struts of the implant may resist bone graft material protrusion from the sides of the web structure and may increase the pressure of the bone graft material. Bone graft material may need to be implanted in a higher-pressure environment to create an environment conducive to strong bone growth (e.g., according to Wolf's law that bone in a healthy person or animal will adapt to the loads it is placed under). The web structure may thus increase the chance of stronger fusion.

Web structures formed from other truss configurations are also contemplated. For example, the trusses may include a series of packing triangles, a two-web truss, a three-web truss, etc. Further, the web structure for an implant may include one or more trusses as described in U.S. Pat. No. 6,931,812 titled "Web Structure and Method For Making the Same", which issued Aug. 23, 2005, which is hereby incorporated by reference in its entirety as though fully and completely set forth herein.

Figure 8:
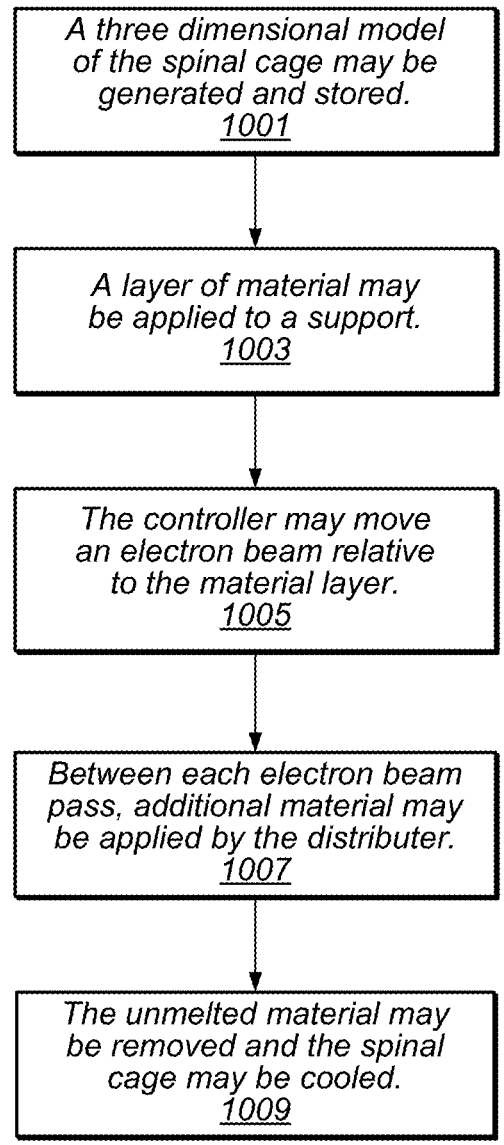
FIG. 8 illustrates a flowchart of a method for making an implant, according to an embodiment.

FIG. 8 illustrates a flowchart of a method for making an implant. In some embodiments, an implant may be made through rapid prototyping (e.g., electron beam melting, laser sintering, etc). It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At 1001, a three dimensional model of an implant is generated and stored in a storage medium accessible to a controller operable to control the implant production process. At 1003, a layer of material (e.g., a powder, liquid, etc.) is applied to a support. In some embodiments, the powder may include γTiAl (γTitanium Aluminides) which may be a high strength/low weight material. Other materials may also be used. The powder may be formed using a gas atomization process and may include granules with diameters approximately in a range of 20 to 200 micrometers (µm) (e.g., approximately 80 µm). The powder may be delivered to the support through a distributer (e.g., delivered from a storage container). The distributer and/or the support may move during distribution to apply a layer (e.g., of powder) to the support. In some embodiments, the layer may be approximately a uniform thickness (e.g., with an average thickness of 20 to 200 micrometers (µm)). In some embodiments, the distributer and support may not move (e.g., the material may be sprayed onto the support). At 1005, the controller moves an electron beam relative to the material layer. In some embodiments, the electron beam generator may be moved, and in some embodiments the support may be moved. If the material is γTiAl, a melting temperature approximately in a range of 1200 to 1800 degrees Celsius (e.g., 1500 degrees Celsius) may be obtained between the electron beam and the material. At 1007, between each electron beam pass, additional material may be applied by the distributer. At 1009, the unmelted material is removed and the implantcooled (e.g., using a cool inert gas). In some embodiments, the edges of the implant may be smoothed to remove rough edges (e.g., using a diamond sander). In some embodiments, the implant may include rough edges to increase friction between the implant and the surrounding bone to increase adhesion of the implant to the bone.

Other methods of making an implant are also contemplated. For example, an implant may be cast or injection molded. In some embodiments, multiple parts may be cast or injection molded and joined together (e.g., through welding, melting, etc). In some embodiments, individual struts forming the implant may be generated separately (e.g., by casting, injection molding, etc.) and welded together to form the implant. In some embodiments, multiple implants of different sizes may be constructed and delivered in a kit. A medical health professional may choose an implant (e.g., according to a needed size) during the surgery. In some embodiments, multiple implants may be used at the implant site.

Specialized tools may be used to insert the implants described herein. Examples of tools that may be used are described in U.S. Published Patent Applications Nos.: 2010/

0161061; 2011/0196495; 20110313532; and 2013/0030529, each of which is incorporated herein by reference.

Figure 9:
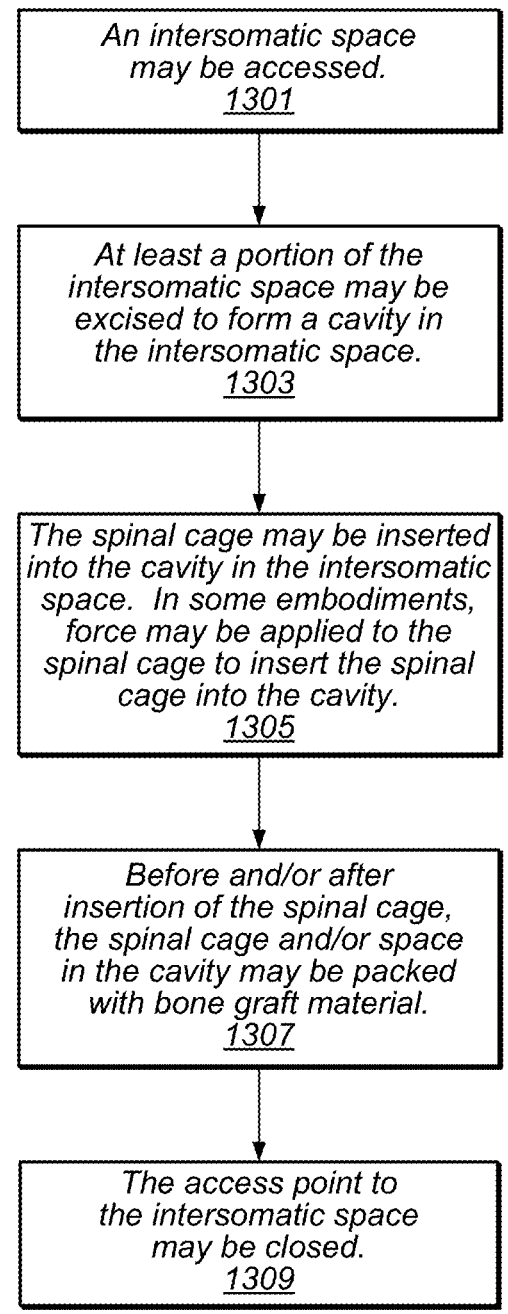
FIG. 9 illustrates a flowchart of a method for implanting a spinal implant, according to an embodiment.

FIG. 9 illustrates a flowchart of a method for implanting a spinal implant, according to an embodiment. It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At step 1301, an intersomatic space is accessed. For example, an anterior opening may be made in a patient's body for an anterior lumbar inter-body fusion (ALIF) approach or a posterior opening may be made for a posterior lumbar inter-body fusion (PLIF) approach. At 1303, at least a portion of the intersomatic space is excised to form a cavity in the intersomatic space. At 1305, the implant is inserted into the cavity in the intersomatic space. In some embodiments, a handler, or some other device, is used to grip the implant. In some embodiments, a force may be applied to the implant (e.g., through a hammer) to insert the implant into the cavity. At 1307, before and/or after insertion of the implant, the implant and/or space in the cavity may be packed with bone graft material. At 1309, the access point to the intersomatic space may be closed (e.g., using sutures).

In some embodiments, the implant may be customized. For example, three dimensional measurements and/or shape of the implant may be used to construct an implant that distributes the web structure throughout a three-dimensional shape design.

In some embodiments, a truss/web structure may be disposed on at least a portion of an implant to facilitate coupling of the implant to an adjacent structure. For example, where an implant is implanted adjacent a bony structure, one or more truss structures may be disposed on and/or extend from a surface (e.g., an interface plate) of the implant that is intended to contact, and at least partially adhere to, the bony structure during use. In some embodiments, such as those including an intervertebral implant disposed between the end plates of two adjacent vertebrae during, one or more truss structures may be disposed on a contact surface of the intervertebral implant to facilitate bone growth that enhances coupling of the intervertebral implant to the bony structure. For example, a truss structure may include one or more struts that extend from the contact surface to define an open space for bone growth therethrough, thereby enabling bone through growth to interlock the bone structure and the truss structure with one another to couple the implant to the bony structure at or near the contact face. Such interlocking bone through growth may inhibit movement between the implant and the bony structure which could otherwise lead to loosening, migration, subsidence, or dislodging of the implant from the intended position. Similar techniques may be employed with various types of implants, including those intended to interface with tissue and/or bone structures. For example, a truss structure may be employed on a contact surface of knee implants, in a corpectomy device, in a hip replacement, in a knee replacement, in a long bone reconstruction scaffold, or in a cranio-maxifacial implant hip implants, jaw implant, an implant for long bone reconstruction, foot and ankle implants, shoulder implants or other joint replacement implants or the like to enhance adherence of the implant to the adjacent bony structure or tissue. Examples of truss structures, and other structures, that may extend from the surface of an implant to facilitate coupling of the implant to an adjacent structure are described in U.S. Published Patent Application No. 2011/0313532, which is incorporated herein by reference.

While implants described herein are depicted as being composed of substantially straight struts, it should be understood that the struts can be non-linear, including, but not limited to curved, arcuate and arch shaped. Examples of implants having non-linear struts are described in U.S. patent application Ser. No. 13/668,968, which is incorporated herein by reference.

Figure 10A:
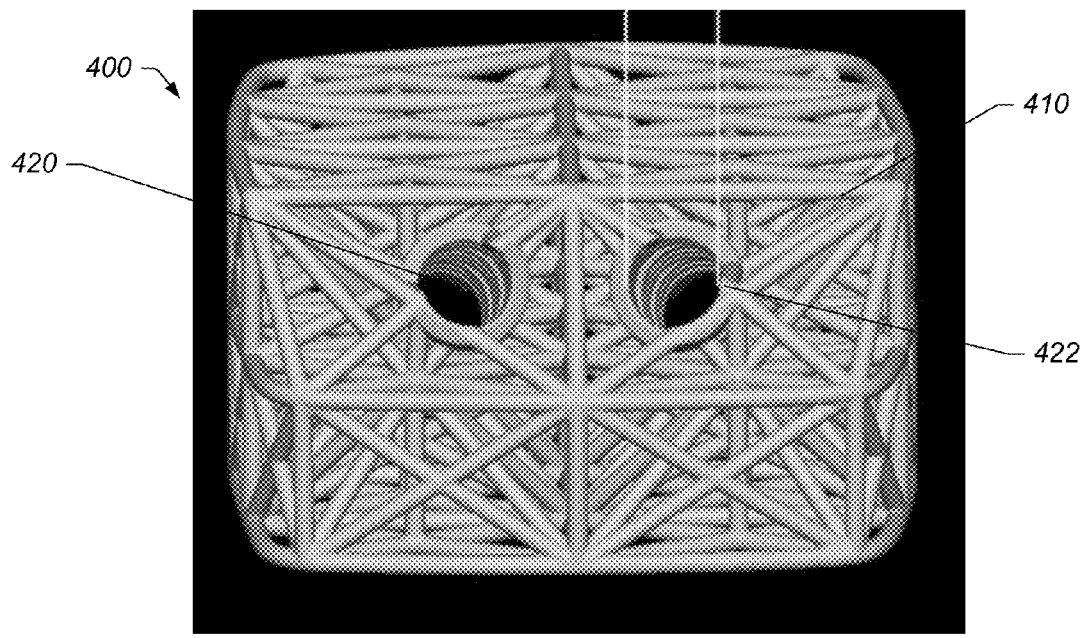
FIGS. 10A-C depict an implant having one or more channels extending through the implant.
Figure 10B:
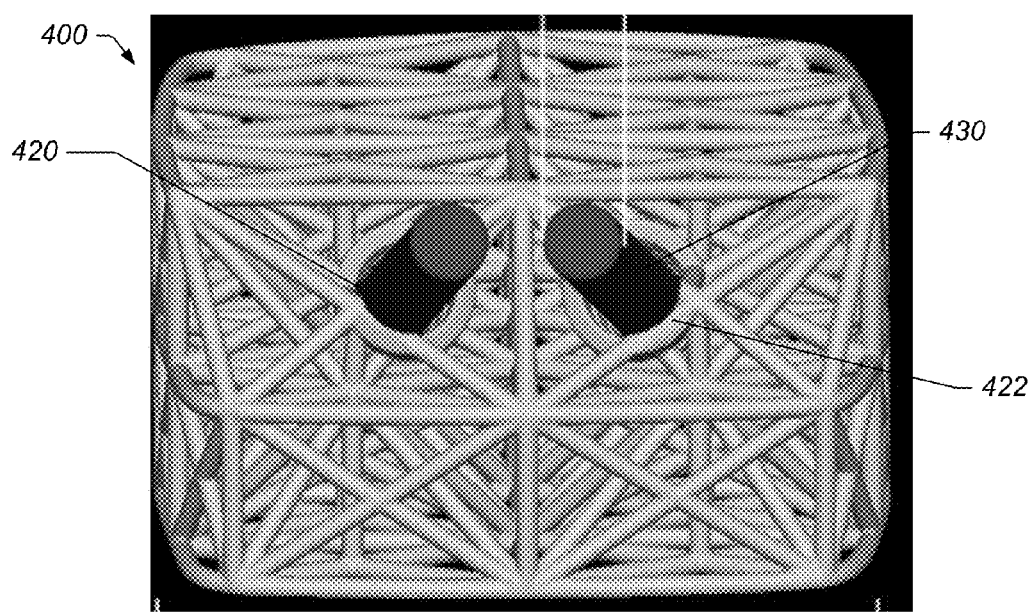
Figure 10C:
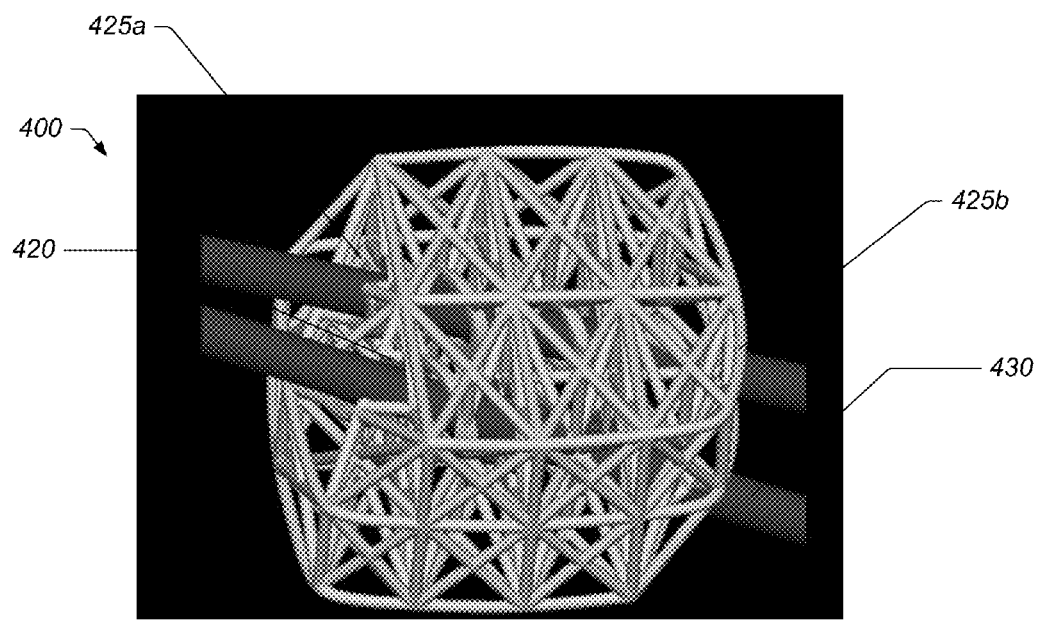

In some embodiments, it is desirable for an implant to be secured to the bone using one or more fasteners (e.g., screws). Fasteners may be coupled to any part of the implant structure to secure the implant to the bone. An embodiment of an implant having one or more channels that can receive a fastener is depicted in FIGS. 10A, 10B, and 10C. In one embodiment, implant 400 is composed of a web structure that includes a space truss 410 formed from two or more planar truss units having a plurality of struts joined at nodes. One or more channels 420 are formed in the web structure. The channels extend through the web structure such that channel exits 425*a,b* are present in at least two sides of the web structure (See FIG. 10C). Channels may be defined by one or more substantially arcuate and/or circular struts 422 coupled to one or more adjacent planar truss units.

The channels may be substantially tubular to receive a cylindrical fastener 430 (e.g., a bone screw). Fastener 430 may move within channel 420 such that the sides of the fastener are not attached to space truss 410. In such embodiments, fastener 430 may include a head (not shown) which contacts a surface of implant 400 to secure the implant to the bone. Alternatively, channels 420 may be substantially threaded, having a threading that is complementary to threading of a bone screw. During use, a bone screw is coupled to channel 420 by mating the bone screw with the threading of the channel. The threading of channel 420, when coupled to the bone screw, help prevent pull out of the fastener from the implant.

Figure 11:
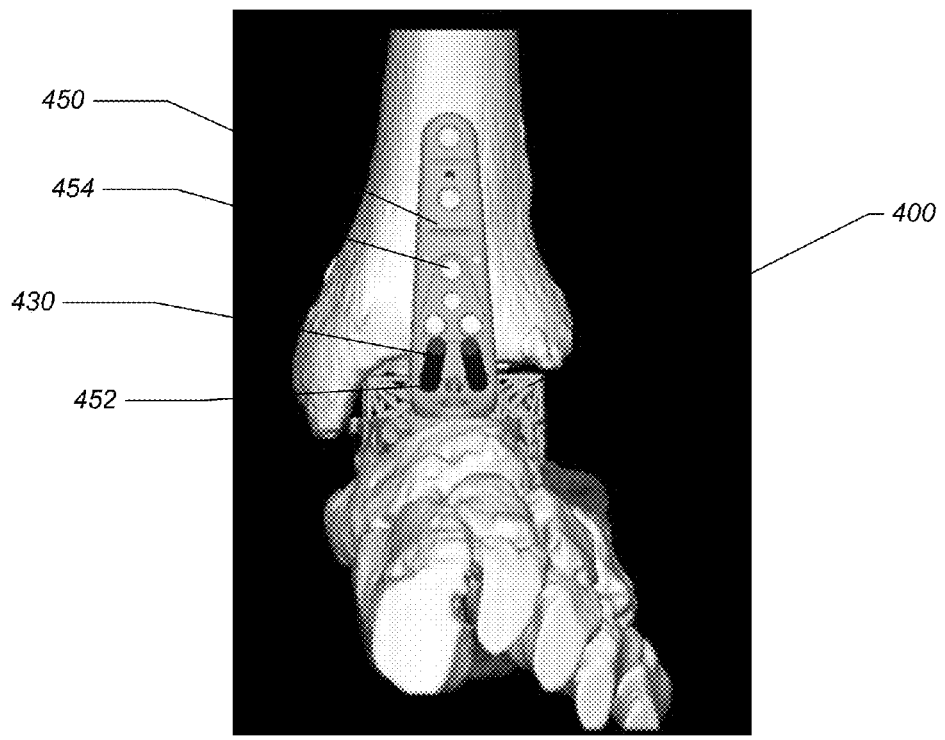
FIG. 11 depicts the implant of FIGS. 10A-C coupled to an external support.

An external support 450 may also be used to secure implant 400 to a bone structure, as depicted in FIG. 11. External support 450 may be coupled to the web structure of implant 400 using one or more fasteners 430. Fasteners 430, therefore, may pass through external support 450, into channels 420 and into a bone structure to secure implant 400 and the external support to the bone. External support 450 may include one or more openings 452 that correspond to the position of channels 420 disposed in implant 400. External support 450 may include additional openings 454, which allow the support to be independently coupled to a bone structure. While depicted as a separate component of the implant system, it should be understood that external support may be integrated with implant 400 to form a unitary implant that includes a space truss attached to an external support.

In one embodiment, a bone structure may be repaired using implant 400. The implant 400 may be placed proximate to, or in contact with, a bone structure in need of repair. Fasteners 430 may be positioned in one or more of channels 420 and coupled to the bone structure. In some embodiments, fasteners 430 are bone screws. A bone screw may be inserted into channels 420 and fastened to the bone by screwing the bone screw into the bone structure. In some embodiments, channels 420 may have threading complementary to the bone screw threading, such that the bone screw is coupled to the implant as well as the bone structure.

In some embodiments, an external support 450 may be used to secure the implant to the bone structure. Implant 400 may be placed proximate to a bone structure. External support 450 may be placed proximate to, or in contact with, implant 400, such that at least some of the openings 452 on external support 450 are aligned with one or more channels 420 of the implant. Fasteners (e.g., bone screws) may be positioned through openings 452 into channels 420, and coupled to the underlying bone structure. Additional fasteners may be positioned in one or more additional openings 454 and coupled to an external portion of the bone structure to provide additional support to the implant.

In an alternate method, external structure 450 may be used as a guide for forming channels in an implant that does not have channels. An implant, such as implant 100, may be positioned proximate to, or in contact with, a bone structure in need of repair. External support 450 may be placed proximate to, or in contact with, a bone structure and implant 100. At least a portion of the openings 452 of external structure 450 are aligned with a portion of the implant. A drill, or other cutting device, may be used to form channels in the implant, using the external support as a guide to determine where the channels are formed. The openings of the external support used to form the channels have a depth sufficient to control the angle that the channel is drilled by providing a guide for the drill bit. The channels of the implant may be custom made during implantation by selecting the external support having openings that will produce channels at the desired location and angle.

Figure 19:
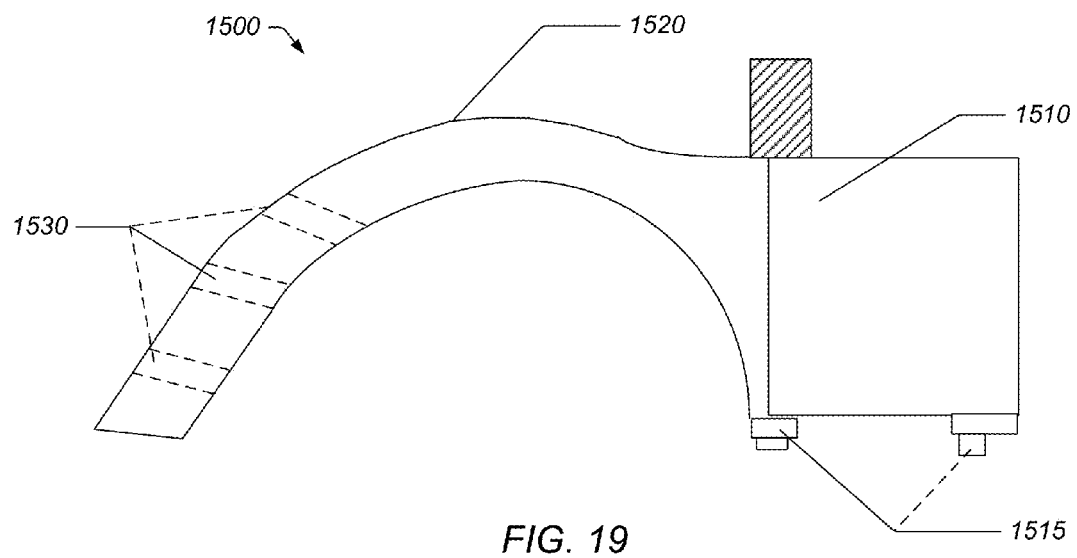
FIG. 19 depicts a trajectory guide device.

In some embodiments, it may be necessary to install the bone screws into the channels of an implant (e.g., implant 400) after the bone screw is passed through a bone structure. Since the implant is positioned within the bone structure before the screws are placed into or through the implant, it would be difficult to achieve the proper alignment of the bone screws with the channels of the implant. FIG. 19 depicts a trajectory guide device 1500, which can be used to direct the placement of one or more bone screws into an implant. Trajectory guide 1500 includes coupling section 1510, and guide 1520. Coupling section includes one or more fasteners 1515, which couple with corresponding fasteners on the implant. The guide 1520 will rest against the skin of the patient and act as a guide, directing the placement of one or more bone screws. Guide 1520 includes one or more channels 1530 through which a bone screw, or other fastening device, is inserted into the subject's skin and underlying bone. The channels are positioned such that a fastener that is inserted through the guide into the subject will be aligned with a channel of the implant.

In an embodiment, an implant 700 includes a distal end 720 and a proximal end 710, wherein the proximal end comprises a space truss 715 comprising two or more planar truss units having a plurality of struts joined at nodes. The space truss is configured to interface with human bone tissue. Distal end 720 includes threading 725 which allows the implant to be screwed into a bone structure. In some embodiments the threaded distal end is substantially solid. The threaded distal end, in some embodiments, is a space truss having exterior threading. Slot 730 may be used to insert the bone screw into a bone structure.

Figure 20:
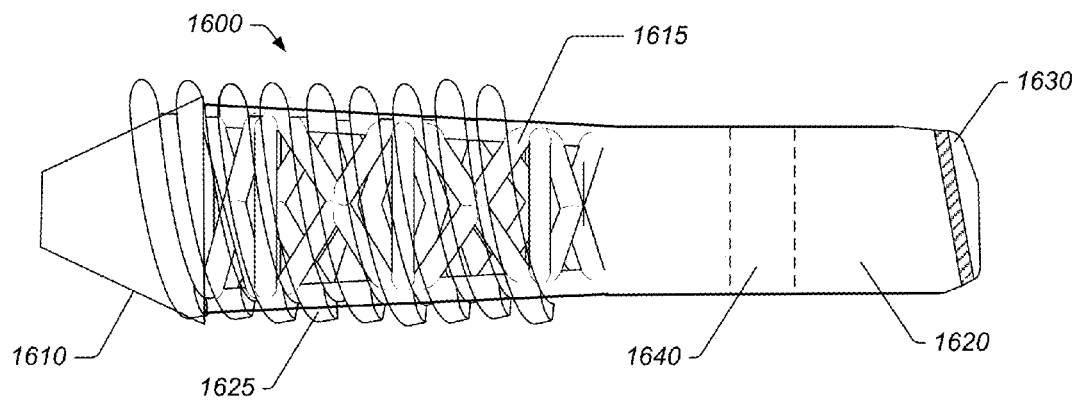
FIG. 20 depicts an embodiment of a bone screw that includes a threaded space-truss proximal end.

FIG. 20 depicts an embodiment of a bone screw 1600 that includes a proximal end 1610 and a distal end 1620. Proximal end 1610 includes a space truss 1615 comprising two or more planar truss units having a plurality of struts joined at nodes. The space truss is configured to interface with human bone tissue. Proximal end 1610 includes threading 1625 which allows the implant to be screwed into a bone structure. Distal end includes a slot 1630 that may be used to insert the bone screw into a bone structure. An opening 1640, or some other connection, that may be used to couple bone screw 1600 to a rod or some other connector (such the bone screw acts as a pedicle screw) is formed in distal end. Opening 1640 is placed in the part of distal end that will extend from the bone after the proximal end is placed into the bone. The use of a truss structure in the proximal end allows the bone screw to be absorbed into the bone structure, providing a more secure connection that a threaded bone screw. The use of a pace truss also helps prevent pullout of the bone screw due to forces placed on the bone screw due to the subjects normal movement.

Figure 21:
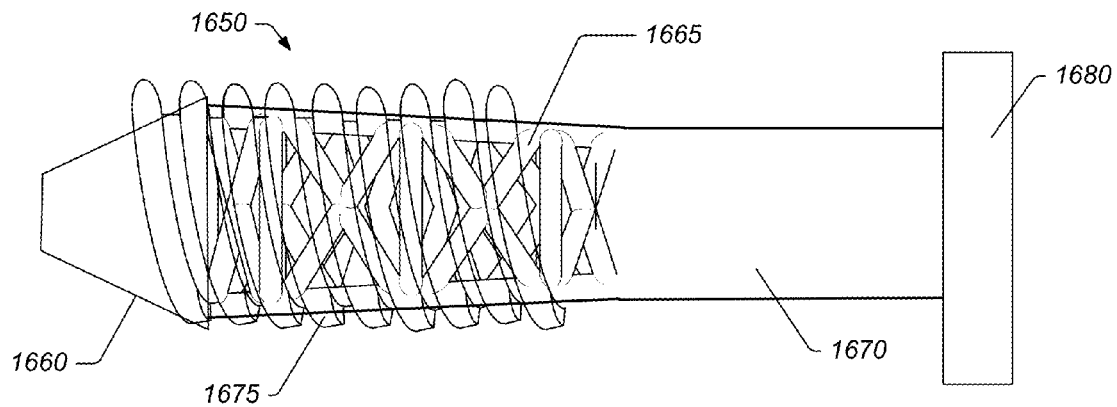
FIG. 21 depicts an embodiment of a bone screw that includes a threaded space-truss proximal end having a cap for engaging bone.

FIG. 21 depicts an embodiment, of a bone screw 1650 that includes a proximal end 1660 and a distal end 1670. Proximal end 1660 includes a space truss 1665 comprising two or more planar truss units having a plurality of struts joined at nodes. The space truss is configured to interface with human bone tissue. Proximal end 1660 includes threading 1675 which allows the implant to be screwed into a bone structure. Distal end includes a head 1680 that may be used to insert couple two bone segments together. During use, head 1680 contacts a bone structure and as proximal end is screwed into the bone, the bone segment in contact with the head is pulled toward the bone segment in which the proximal head is embedded.

Figure 22:
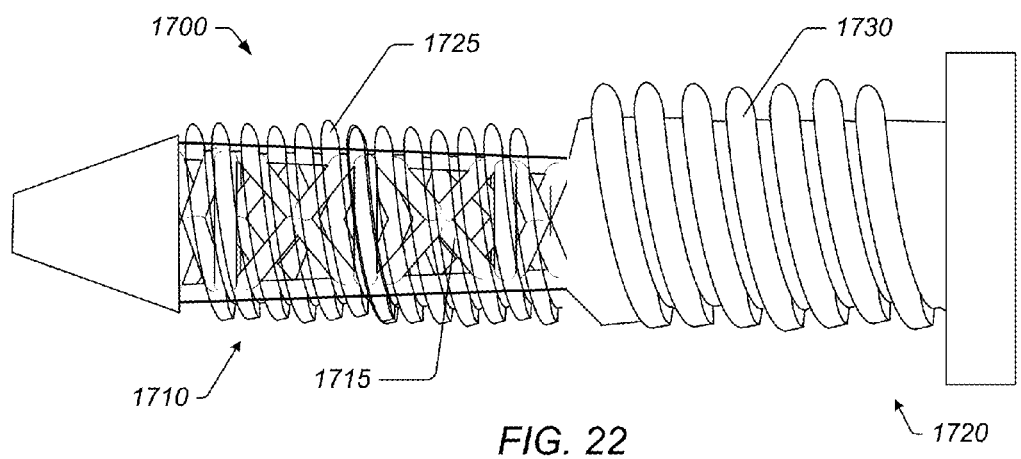
FIG. 22 depicts an embodiment of a bone screw that includes a threaded space-truss proximal end and a threaded distal end.

FIG. 22 depicts an embodiment of a bone screw 1700 that includes a proximal end 1710 and a distal end 1720. Proximal end 1710 may include a space truss 1715 or may be substantially solid (not shown). When present, a space truss is configured to interface with human bone tissue. Proximal end 1710 includes threading 1725 having a first pitch which allows the implant to be screwed into a bone structure. Distal end also includes threading 1730 having a second pitch which is different from the threading on the proximal end. Bone screw 1700 may be used to couple two bone segments together. During use, a pilot hole is drilled through a first bone structure that allows proximal end 1710 to be passed through first bone structure. The proximal end is then brought into contact with a second bone segment and is screwed into the second bone segment. As the proximal end is screwed into the second bone segment, the threads on the distal end engage the first bone segment, drawing the second bone segment toward the first bone segment. When fully inserted into the second bone segment, bone screw 1700 holds the two bone structures in contact with each other.

Figure 12A:
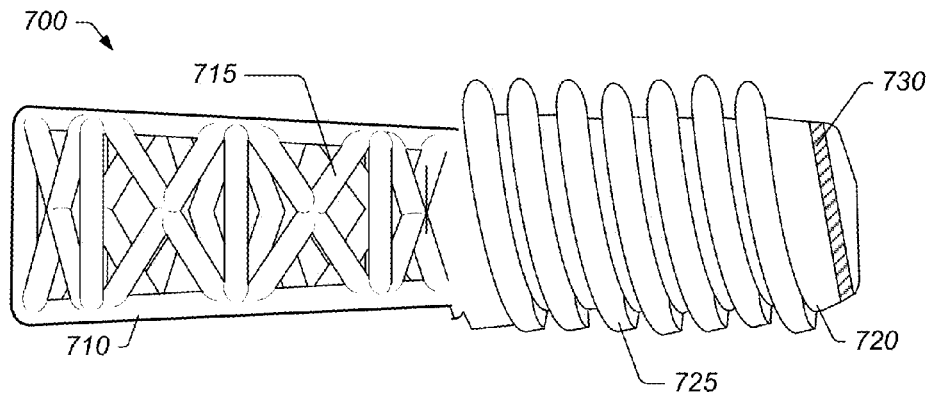
FIG. 12A-B depict implants having external threading.
Figure 12B:
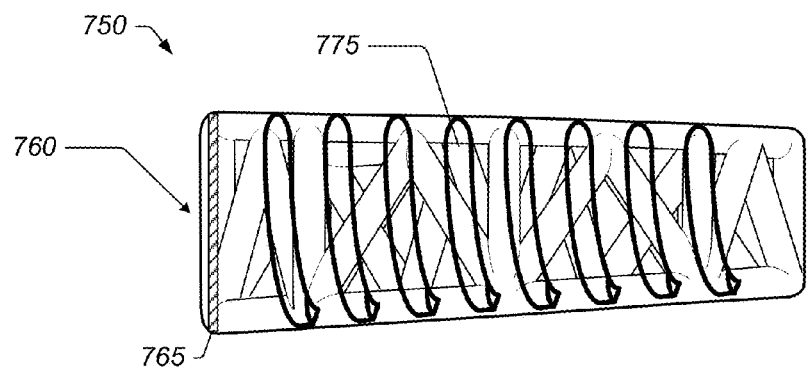

In an alternate embodiment, an entire bone screw may be formed from a web structure to allow the bone screw to be absorbed by the bone during use. FIG. 12B depicts an embodiment of a bone screw 750. Bone screw 750 is composed of a space truss 755 comprising two or more planar truss units having a plurality of struts joined at nodes. Space truss 755 is configured to interface with human bone tissue. Threading 775 is positioned around space truss allowing the bone screw to be screwed into a bone structure. End 760 includes a slot 765, or some other structure or shape that allows a fastening tool (e.g., a screwdriver) to couple with the distal end. The fastening tool is used to secure threading 775 into the bone structure by allowing a user to rotate bone screw 750. As depicted bone screw has threading coupled to space truss 755. However, it should be understood that one or more of the truss units of space truss 755 may have one or more curved struts that together form threading 775.

Bone screw 750 may be inserted into a bone structure by forming an opening in the bone structure sufficient to at least act as a pilot hole for the bone screw. The bone screw is placed in contact with the opening and rotated by coupling a fastening tool onto the end (e.g., through slot 765).

Rotation of bone screw 750, allows the threads to contact the bone structure, securing the implant into the bone structure. Bone screw 750 may be used for a variety of bone structures including but not limited to hip, knee, shoulder, elbow, spine bone structures.

Proximal humeral fractures remain a challenge to repair because of fragment comminution, poor bone quality, and the complexity of the anatomy to be reconstructed. Various osteosynthesis devices are available for displaced fractures, for example, Kirschner wires, plates and screws, intramedullary nails, low-profile plates with fixed-angle locking plates, and anatomic or inverse humera prostheses. However, the outcome of these procedures is inconsistent and depends largely on the surgical technique used and the surgeon's skill.

Figure 13:
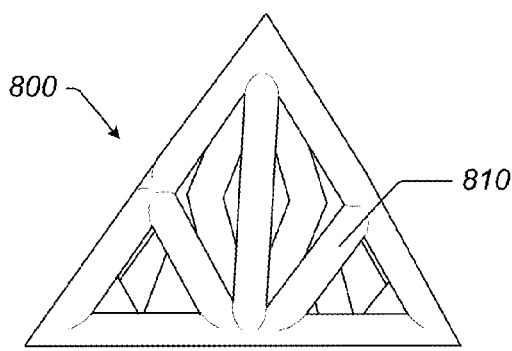
FIG. 13 depicts an implant for treatment of complex fractures of the proximal humerus.

In an embodiment, depicted in FIG. 13, an osteosynthesis implant 800 may be used for the treatment of complex fractures of the proximal humerus. Implant 800 is a triangular prism which is composed of a planar truss 810. It is inserted in the proximal humeral cavity to stabilize the humeral head and tuberosities. The space truss structure improves the osteointegration of the device compared to other similar implants.

Figure 14:
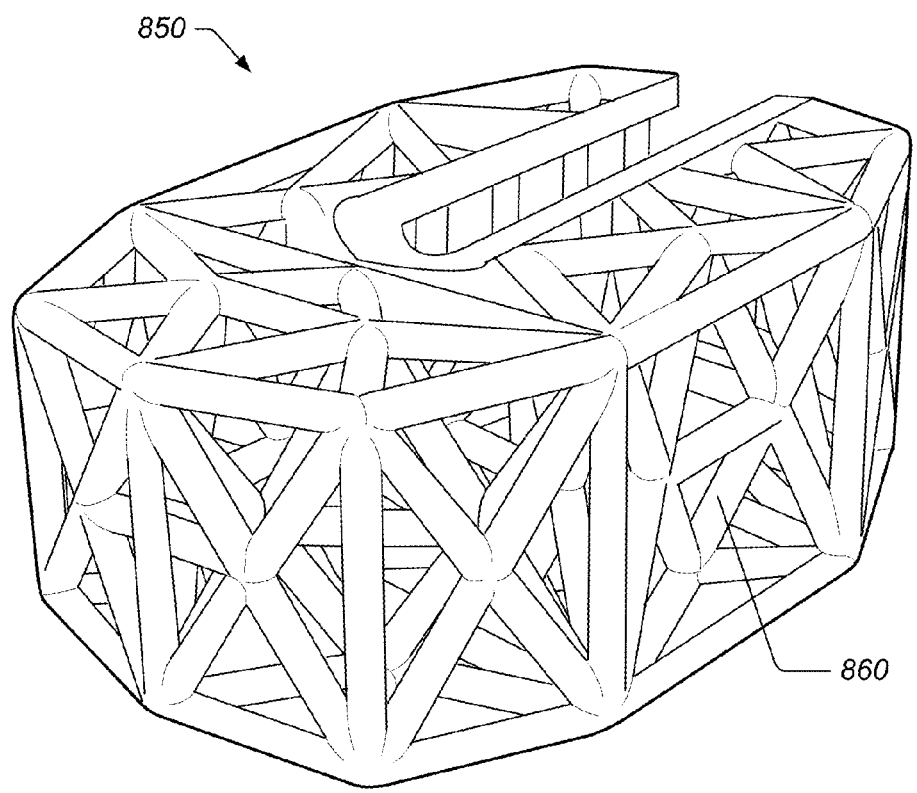
FIG. 14 depicts an implant used for revisions of failed total ankle replacements.

In an embodiment, depicted in FIG. 14, an osteosynthesis implant 850 may be used for revisions of failed total ankle replacements. Implant 850 may be used to bridge structural defects left behind by the removal of the total ankle prosthesis. Implant 850 is a block having a U-shaped cutout which is composed of a planar truss 860.

Figure 15:
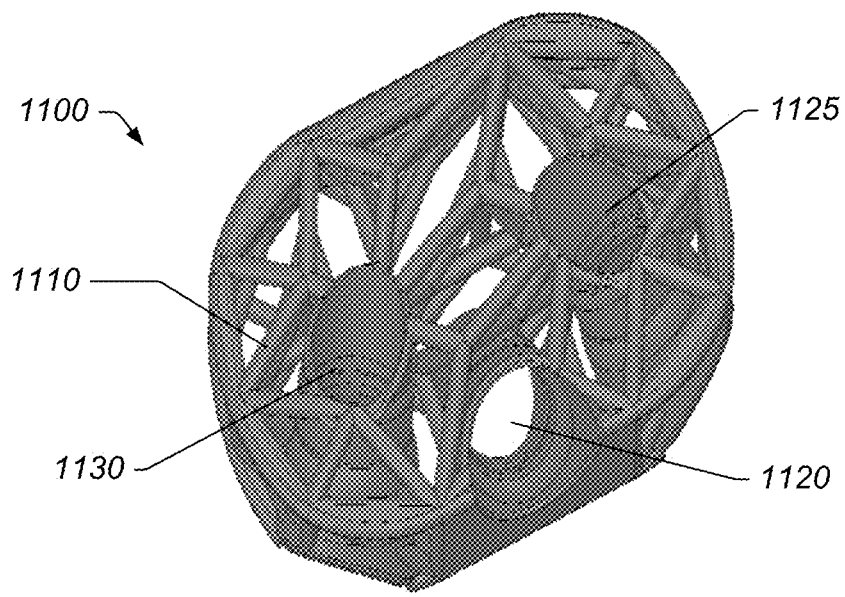
FIG. 15 depicts an embodiment of an implant having three channels.

FIG. 15 depicts an embodiment of an implant having one or more channels that can receive a fastener. In one embodiment, implant 1100 is composed of a web structure that includes a space truss 1110 formed from two or more planar truss units having a plurality of struts joined at nodes. One or more channels 1120 are formed in the web structure. The channels extend through the web structure such that channel exits are present in at least two sides of the web structure. Channels may be defined by a channel structure 1125 coupled to one or more adjacent planar truss units.

The channels may be substantially tubular to receive a cylindrical fastener (e.g., a bone screw). A fastener may move within channel 1120 such that the sides of the fastener are not attached to space truss 1110. In such embodiments, a fastener may include a head (not shown) which contacts a surface of implant 1100 to secure the implant to the bone. Alternatively, channel structures 1125 may include threading 1130 that is complementary to threading of a bone screw. During use, a bone screw is coupled to channel 1120 by mating the bone screw with the threading of the channel. The threading of channel 1120, when coupled to the bone screw, help prevent pull out of the fastener from the implant.

Figure 16:
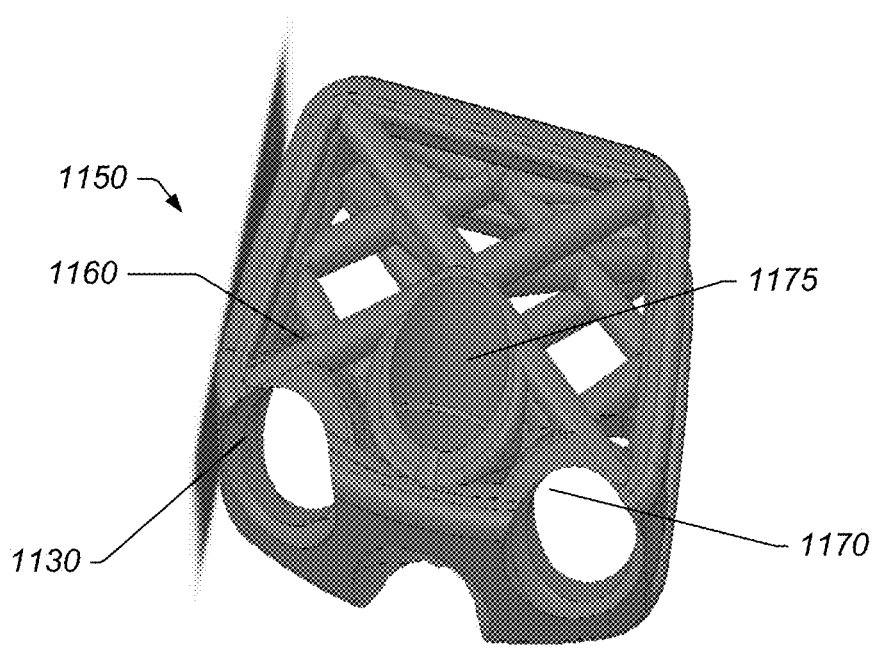
FIG. 16 depicts an alternate embodiment of an implant having three channels.

FIG. 16 depicts an embodiment of an implant having one or more channels that can receive a fastener. In one embodiment, implant 1150 is composed of a web structure that includes a space truss 1160 formed from two or more planar truss units having a plurality of struts joined at nodes. One or more channels 1170 are formed in the web structure. The channels extend through the web structure such that channel exits are present in at least two sides of the web structure. Channels may be defined by a channel structure 1175 coupled to one or more adjacent planar truss units.

The channels may be substantially tubular to receive a cylindrical fastener (e.g., a bone screw). A fastener may move within channel 1170 such that the sides of the fastener are not attached to space truss 1160. In such embodiments, a fastener may include a head (not shown) which contacts a surface of implant 1150 to secure the implant to the bone. Alternatively, channel structures 1175 may include threading 1180 that is complementary to threading of a bone screw. During use, a bone screw is coupled to channel 1170 by mating the bone screw with the threading of the channel. The threading of channel 1170, when coupled to the bone screw, help prevent pull out of the fastener from the implant.

Figure 17:
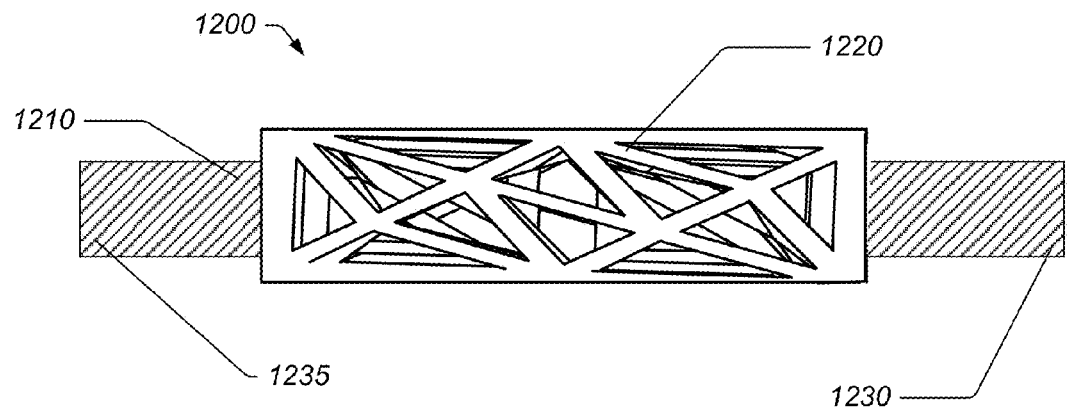
FIG. 17 depicts an embodiment of a bone rod connected to a space truss.

In some fractures of the long bones, the best way to align the bone ends is by inserting a rod or nail through the hollow center of the bone that normally contains some marrow. Most bone rods, however, are poorly adsorbed by the bone, being typically formed from a bio-inert material. In an embodiment, depicted in FIG. 17, an implant 1200 includes a bone rod 1210 at least partially encompassed by a space truss 1220. During use, ends 1230 and 1235 of implant 1200 may be inserted into the bone. Space truss 1220 may also be inserted into the bone, or may occupy an empty space between the broken bone pieces. Space truss 1220 allows better integration of the bone rod into the subjects bone structure.

Figure 18:
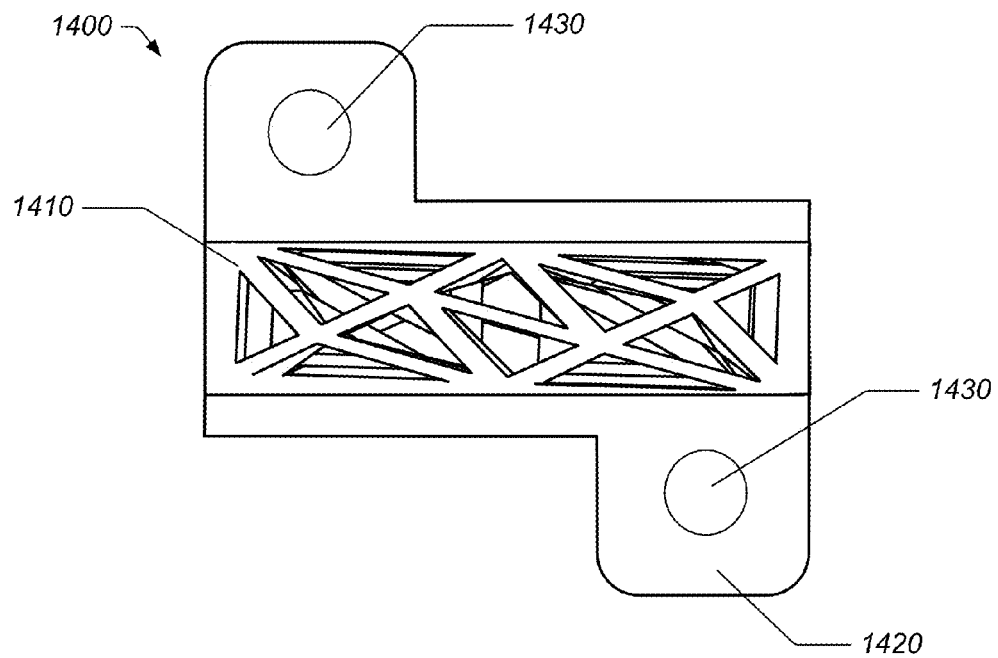
FIG. 18 depicts a top-view of an embodiment of an implant which includes a web structure connected to a plate.

FIG. 18 depicts a top-view of an embodiment of an implant 1400 which includes a web structure 1410 connected to a plate 1420. Plate 1420 includes one or more screw holes 1430 which allow a bone screw to be used to secure implant 1400 to an exterior of the bone. In use, web structure 1410 may be placed is a space formed in a bone, a natural space (e.g., as a spinal disk replacement device, or between two separated bone segments. In any application, plate 1420 will rest on the exterior of the bone, and provides two screw holes 1430 that allow the user to secure the implant to the bone. In this manner, the implant is less likely to be pulled from the bone section during normal movement of the subject.

Figure 23:
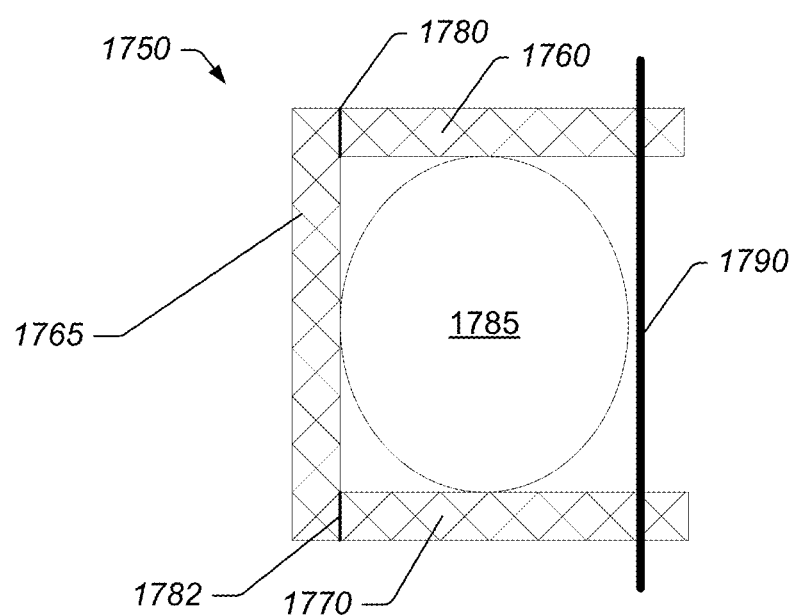
FIG. 23 depicts a schematic diagram of a truss cast used to form an exterior support for fractured bone structure.

FIG. 23 depicts a schematic diagram of a truss cast used to form an exterior support for fractured bone structure. In an embodiment truss cast comprises a single truss structure or a plurality of space trusses coupled to each other. The truss cast is formed so that the it can be wrapped around the fractured bone, acting as a cast to hold the fractured bone segments in place. In the embodiment depicted in FIG. 23, truss cast 1750 includes three space trusses 1760, 1765 and 1770. Space trusses are coupled to each other using flexible connectors 1780 and 1782. Flexible connectors allow the space trusses to be rotated, with respect to each other, by at least 90 degrees. Truss cast 1750 includes a connector 1790 which extends from first space truss 1760 to third space truss 1770. In use, truss cast is wrapped around bone 1785 at the site of the fracture. Connector is fastened to space truss 1760 and 1770 to hold truss cast in place. In an embodiment, connector may include a tensioning device that draws the two space trusses 1760 and 1770 together to secure the truss cast against the bone. It should be understood that while the truss cast is depicted as having three space trusses, more or less space trusses may be used. In one embodiment, a single space truss is used as a truss cast. The single space truss may be formed of a substantially flexible material that allows the space truss to be pulled around the fractured bone segment by tensioning of the connector.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

In accordance with the above descriptions, in various embodiments, an implant may include a web structure. The web structure for the implant may include a micro truss design. In some embodiments, the micro truss design may include a web structure with multiple struts. Other web structures are also contemplated. The web structure may extend throughout the implant (including a central portion of the implant). The web structure may thus reinforce the implant along multiple planes (including internal implant load bearing) and provide increased area for bone graft fusion. The web structure may be used in implants such as spinal implants, corpectomy devices, hip replacements, knee replacements, long bone reconstruction scaffolding, and cranio-maxifacial implants. Other implant uses are also contemplated. In some embodiments, the web structure for the implant may include one or more geometric objects (e.g., polyhedrons). In some embodiments, the web structure may not include a pattern of geometrical building blocks (e.g., an irregular pattern of struts may be used in the implant). In some embodiments, the web structure may include a triangulated web structure including two or more tetrahedrons. A tetrahedron may include four triangular faces in which three of the four triangles meet at each vertex. The web structure may further include two tetrahedrons placed together at two adjacent faces to form a web structure with a hexahedron-shaped frame (including six faces). In some embodiments, multiple hexahedron-shaped web structures may be arranged in a side-by-side manner. The web structures may connect directly through side vertices (e.g., two or more hexahedron-shaped web structures may share a vertex). In some embodiments, the web structure may be angled to provide lordosis to the implant.

Further modifications and alternative embodiments of various aspects of the invention may be apparent to those skilled in the art in view of this description. For example, although in certain embodiments, struts have been described and depicts as substantially straight elongated members, struts may also include elongated members curved/arched along at least a portion of their length. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. Furthermore, it is noted that the word "may" is used throughout this application in a permissive sense (i.e., having the potential to, being able to), not a mandatory sense (i.e., must). The term "include", and derivations thereof, mean "including, but not limited to". As used in this specification and the claims, the singular forms "a", "an" and "the" include plural referents unless the content clearly indicates otherwise. Thus, for example, reference to "a strut" includes a combination of two or more struts. The term "coupled" means "directly or indirectly connected".

What is claimed is:

1. An implant for interfacing with a bone structure, comprising:
   a web structure comprising a space truss comprising two or more planar truss units having a plurality of struts joined at nodes, wherein the space truss comprises planar truss units forming one or more polyhedron truss units, and wherein at least one polyhedron truss unit of the web structure passes into a central portion of the implant, and wherein the web structure is configured to interface with human bone tissue; and
   one or more cylindrical channels extending through the space truss, the one or more cylindrical channels having channel exits in at least two sides of the web structure.

2. The implant of claim 1, wherein one or more of the channels are defined by one or more circular or arcuate struts coupled to one or more planar truss units.

3. The implant of claim 1, wherein one or more of the channels are defined by channel structure coupled to one or more of the planar truss units.

4. The implant of claim 1, wherein one or more of the channels are substantially threaded, having a threading complementary to the threading of a bone screw fastener.

5. The implant of claim 1, wherein the one or more channels are defined by one or more substantially arcuate and/or circular struts coupled to one or more planar truss units.

6. The implant of claim 1, wherein the plurality of planar truss units comprise one or more planar triangular truss units having three substantially straight struts and three nodes in a triangular configuration.

7. The implant of claim 1, wherein the plurality of planar truss units are coupled to one another such that one or more planar truss units lie in a plane that is not substantially parallel to a plane of a planar truss unit that shares at least one strut with the one or more planar truss units.

8. The implant of claim 1, wherein a plurality of planar truss units define an exterior surface of the web structure.

9. The implant of claim 1, wherein the at least some of the connecting struts define triangular trusses having at least one node shared by two different triangular planar truss units having different corresponding angles.

10. The implant system of claim 9, further comprising an external support couplable to the web structure using one or more of fasteners, wherein, during use, the external support is couplable to an exterior of the bone structure.

11. The implant system of claim 10, wherein the external support comprises one or more openings that align with one or more of the channels of the implant such that, during use, a fastener may pass through the one or more openings of the external support into one or more channels of the implant.

12. The implant system of claim 10, wherein the external support is an integral part of the web structure.

13. The implant system of claim 11, wherein the external support comprises one or more additional openings that accept a fastener that is used to couple the external support to an external portion of the bone structure.

14. The implant of claim 1, wherein the plurality of planar truss units comprises a first planar triangular truss unit coupled to a second planar triangular truss unit, wherein the first and second planar triangular truss units are coupled in an opposing manner with a single node defining the apex of each planar triangular truss unit.

15. An implant system for interfacing with a bone structure, comprising:
   a web structure comprising a space truss comprising two or more planar truss units having a plurality of struts joined at nodes, wherein the space truss comprises planar truss units forming one or more polyhedron truss units, and wherein at least one polyhedron truss unit of the web structure passes into a central portion of the implant, and wherein the web structure is configured to interface with human bone tissue;

one or more cylindrical channels extending through the space truss, the one or more cylindrical channels having a channel entrance on at least one side of the web structure and a channel exit on at least one different side of the web structure; and one or more fasteners positionable within the channels, wherein the fasteners couple the web structure to a bone during use.

* * * * *